United States Patent
Boyer et al.

(10) Patent No.: US 9,532,569 B2
(45) Date of Patent: Jan. 3, 2017

(54) STRIGOLACTONE ANALOGUES AND THE USE THEREOF FOR THE TREATMENT OF PLANTS

(71) Applicants: INSTITUT NATIONAL DE LA RECHERCHE AGRONOMIQUE, Paris (FR); CENTRE NATIONAL DE LA RECHERCHE SCIENTIFIQUE, Paris (FR); UNIVERSITE DE PARIS XI PARIS SUD, Orsay (FR)

(72) Inventors: Francois-Didier Boyer, Le Chesnay (FR); Catherine Rameau, Paris (FR); Jean-Paul Pillot, Versailles (FR); Vincent Servajean, Meudon la Foret (FR); Alexandre De Saint Germain, Saint Cloud (FR); Jean-Marie Beau, Menestreau en Vilette (FR); Jean-Bernard Pouvreau, Nantes (FR); Guillaume Clave, Elancourt (FR)

(73) Assignees: INSTITUT NATIONAL DE LA RECHERCHE AGRONOMIQUE, Paris (FR); CENTRE NATIONAL DE LA RECHERCHE SCIENTIFIQUE, Paris (FR); UNIVERSITE DE PARIS XI PARIS SUD, Orsay (FR)

( * ) Notice: Subject to any disclaimer, the term of this patent is extended or adjusted under 35 U.S.C. 154(b) by 47 days.

(21) Appl. No.: 14/403,132

(22) PCT Filed: May 23, 2013

(86) PCT No.: PCT/EP2013/060624
§ 371 (c)(1),
(2) Date: Nov. 21, 2014

(87) PCT Pub. No.: WO2013/174925
PCT Pub. Date: Nov. 28, 2013

(65) Prior Publication Data
US 2015/0141255 A1 May 21, 2015

(30) Foreign Application Priority Data

May 23, 2012 (FR) .................................... 12 54700

(51) Int. Cl.
*A01N 43/08* (2006.01)
*A01N 43/16* (2006.01)
(Continued)

(52) U.S. Cl.
CPC ............... *A01N 43/08* (2013.01); *A01N 43/16* (2013.01); *C07D 307/56* (2013.01);
(Continued)

(58) Field of Classification Search
CPC ...... A01N 43/08; A01N 43/16; C07D 307/56; C07D 307/58; C07D 307/60; C07D 307/64; C07D 307/68; C07D 407/12
See application file for complete search history.

(56) References Cited

U.S. PATENT DOCUMENTS 8,822,383 B2 * 9/2014 Sasaki .................... A01N 47/18
504/299
2011/0230352 A1 * 9/2011 Rameau ................. A01N 43/12
504/297

FOREIGN PATENT DOCUMENTS

WO 2010/137662 A1 12/2010
WO WO2010/137662 A1 * 12/2010 ........... C07D 306/60
(Continued)

OTHER PUBLICATIONS

Fukui et al., "New branching inhibitors and their potential as strigolactone mimics in rice," 2011; Bioorg. & Med. Chem. Lett., 21:4905-4908.*
(Continued)

*Primary Examiner* — Jane C Oswecki
(74) *Attorney, Agent, or Firm* — Im IP Law PLLC; C. Andrew Im

(57) ABSTRACT

A compound of general formula (I):

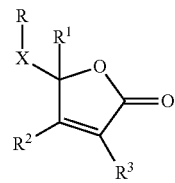

in which X represents O, S, NH or an N-alkyl radical, $R^1$ and $R^2$, identical or different, each represent H or a $C_1$-$C_{10}$ hydrocarbon radical, $R^1$ and $R^2$ not both representing H, $R^3$ represents a $C_1$-$C_{10}$ hydrocarbon radical, and R represents a phenyl radical monosubstituted or disubstituted by a substituent Y and, if applicable, a substituent Z, chosen from Cl, Br, I and $CF_3$, or R represents a C=$R^4(R^5)$ radical in which $R^4$ represents an hydrocarbon radical and $R^5$ represents a linear or branched, saturated or unsaturated, hydrocarbon radical, optionally substituted, a $COR^6$ group or a $CO_2R^6$ group, where $R^6$ represents a hydrogen atom or a linear or branched, saturated or unsaturated, hydrocarbon radical. This compound can be used for the treatment of higher plants for controlling their growth and architecture.

33 Claims, 6 Drawing Sheets

(51) Int. Cl.
| | | |
|---|---|---|
| C07D 307/56 | (2006.01) | |
| C07D 307/58 | (2006.01) | |
| C07D 307/60 | (2006.01) | |
| C07D 407/12 | (2006.01) | |
| C07D 307/64 | (2006.01) | |
| C07D 307/68 | (2006.01) | |

(52) U.S. Cl.
CPC ......... *C07D 307/58* (2013.01); *C07D 307/60* (2013.01); *C07D 307/64* (2013.01); *C07D 307/68* (2013.01); *C07D 407/12* (2013.01)

(56) References Cited

FOREIGN PATENT DOCUMENTS

| WO | 2012/043813 A1 | 4/2012 | |
|---|---|---|---|
| WO | WO2012/043813 A1 * | 5/2012 | ........... C07D 307/60 |
| WO | WO2012/146374 A2 * | 11/2012 | ........... C07D 307/58 |

OTHER PUBLICATIONS

"Alkyl radical", The Free Dictionary [online], [retrieved Apr. 4, 2016] Retrieved from the Internet: <URL: http://www.thefreedictionary.com/alkyl+radical>.*

Benharrat et al., "Virulence diversity among branched broomrape (*O-ramosa* L) populations in France", Agron Sustain. Dev., 2005, pp. 123-128, vol. 25, No. 1.

Beveridge et al., "The rms1 Mutant of Pea Has Elevated Indole-3-Acetic Acid Levels and Reduced Root-Sap Zeatin Riboside Content but Increased Branching Controlled by Graft-Transmissible Signal(s)," Plant Physiol., 1997, pp. 1251-1258, vol. 115.

Canevet et al., "Reactions de Friedel-Crafts de Derives Aromatiques sur des Composes Dicarbonyles-1,4 Ethyleniques-2,3.II Alkylations par Quelques Hydroxy-5 ou Chlor-5 Dihydro-,5 Furannones-2. Nouvelle Methode de Synthese des Acides 1H-Indenecarboxyliques-1," Tetrahedron, 1978, pp. 1935-1942, vol. 34.

Dos Santos et al., "Defense Gene Expression Analysis of Arabidopsis thaliana Parasitized by Orobanche ramosa," Phytopathology, 2003, pp. 451-457, vol. 93, No. 4.

Fukui et al., "New branching inhibitors and their potential as strigolactone mimics in rice," Bioorg. Med. Chem. Lett., 2011, pp. 905-4908, vol. 21, Elsevier Ltd.

Johnson et al., "The Preparation of Synthetic Analogs of Strigol," Journal of the Chemical Society-Perkin Transactions, 1981, pp. 734-1743, vol. 1.

Johnson et al., "Branching Genes are Conserved across Species. Genes Controlling a Novel Signal in Pea are Coregulated by Other Long-Distance Signals," Plant Physiol., 2006, pp. 1014-1026, vol. 142.

Mangnus et al., "Improved Synthesis of Strigol Analog GR24 and Evaluation of the Biological-Activity of Its Diastereomers," J. Agric. Food Chem., 1992, pp. 1230-1235, vol. 40.

Nair et al., "Degenerative Chemistry of Malondialdehyde—Structure, Stereochemistry, and Kinetics of Formation of Enaminals from Reaction with Amino-Acids," J. Am. Chem. Soc., 1981, pp. 3030-3036, vol. 103.

Timonen et al., "Synthesis and anti-inflammatory effects of a series of novel 7-hydroxycoumarin derivatives," Eur. J. Med. Chem., 2011, pp. 3845-3850, vol. 46, Elsevier Masson SAS.

* cited by examiner

STRIGOLACTONE ANALOGUES AND THE USE THEREOF FOR THE TREATMENT OF PLANTS

RELATED APPLICATIONS

This application is a §371 application from PCT/EP2013/060624 filed May 23, 2013, which claims priority from French Patent Application No. 12 54700 filed May 23, 2012, each of which is herein incorporated by reference in its entirety.

TECHNICAL FIELD OF THE INVENTION

The present invention relates to novel compounds capable of controlling the branching of higher plants, to a composition comprising such compounds, and to the use thereof for the treatment of higher plants, in particular with a view to controlling the branching thereof, by selective or overall inhibition of bud growth on the plant. This inhibition can be temporary, in such a way as to control the period of development of these buds, or permanent, in order, for example, to promote the growth of other parts of the plant to the detriment of that or those inhibited.

The compounds according to the invention are particularly useful in the agricultural field, for the culturing of plants, such as food plants, leguminous plants, forest plants, ornamental plants, etc., for which the control of the number of branches, of the initiation of buds and/or of the branching period can improve the yield and/or the quality of the production (fruit size, wood quality, etc.). The term "higher plants" is intended to mean vascular multicellular plants which have roots and an aerial part. The term "culturing" is intended to mean both culturing in the field and implantations for forests, and in vitro culture, soilless culture, or the like.

BACKGROUND OF THE INVENTION

Cultivated plants, whether they are cultivated for their flowers, their fruits, their seeds or their vegetative parts, are the subject of numerous controls and treatments, so as to obtain the best possible yield and the best quality.

Thus, for example, it is attempted to control the flowering periods so as to avoid flower buds being initiated during periods where there is a high risk of frost. Likewise, when it is desired to obtain large size fruits, or more generally more vigorous plants, the plant is pruned so as to limit the number of branches and thus the number of "storage" organs represented by fruits in the swelling period or seeds undergoing filling. The use of fertilizer also makes it possible to optimize the yields.

Such controls and treatments require a knowledge not only of the plant itself, but of the conditions under which it is cultivated: nature of the soil, climate, etc., in particular in order to know when and how to prune the plants. Moreover, pruning is an expensive, tedious process which requires the intervention of qualified individuals.

In order to remedy these drawbacks, the prior art has proposed processes for the chemical treatment of plants in order to control their growth, by definitive or temporary and total or partial inhibition of the growth of the branches, so as in particular to optimize the yield of these plants.

In particular, it has been proposed in patent document FR-A-2 930 402 to bring the plants to be treated into contact with a solution containing a natural or synthetic strigolactone, so as to inhibit or limit the growth of all or part of the branches.

Strigolactones are plant hormones of the apocarotenoid family. They are principally composed of a backbone comprising four rings termed A, B, C and D, more specifically of a tricyclic lactone ABC connected, via an enol ether bond, to a butyrolactone ring termed ring D. Numerous natural strigolactones, such as sorgolactone, 5-deoxystrigol, strigol, orobanchol, 2'-epi-orobanchol, solanacol, orobanchyl acetate or strigyl acetate, and synthetic strigolactones, such as GR24 or GR5, are currently known. Applications of strigolactones have been described not only for controlling the growth and architecture of higher plants, but also for inducing germination of the seeds of parasitic plants such as *Orobanche* plants. In order to remove said parasitic plants from agricultural soils, it is thus proposed to treat said soils with strigolactones, so as to induce the germination of the parasitic plants in the absence of host plants essential to their existence, thereby leading to their death.

Among the strigolactones, the molecule termed GR24, of formula:

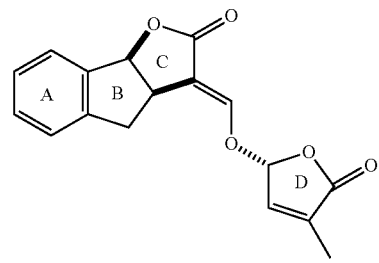

in which the ring A is an aromatic ring,
and the molecule termed GR5, of formula:

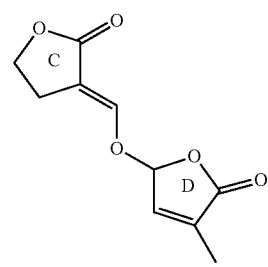

devoid of rings A and B,
have been described by the prior art as particularly effective for repressing the branching of higher plants. Besides the fact that these compounds are not very easy to synthesize, they have, however, the drawback of being relatively cytotoxic.

OBJECT AND SUMMARY OF THE INVENTION

The present invention aims to provide novel compounds which can be used in plant treatment processes, and which are at least as effective as natural strigolactones, and preferably as the synthetic strigolactones proposed by the prior art, in terms of controlling the degree of branching of plants, while being simpler to synthesize and having in particular less cytotoxicity.

To this effect, novel compounds are proposed according to the invention, said novel compounds corresponding to general formula (I):

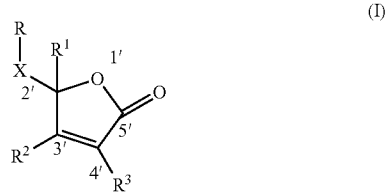

(I)

in which:
X represents an oxygen atom, a sulfur atom, NH or an N-alkyl radical,
$R^1$ and $R^2$, which may be identical or different, each represent a hydrogen atom or a linear or branched, saturated or unsaturated, $C_1$-$C_{10}$ hydrocarbon-based radical, $R^1$ and $R^2$ not both representing a hydrogen atom,
$R^3$ represents a linear or branched, saturated or unsaturated, $C_1$-$C_{10}$ hydrocarbon-based radical,
and R represents a phenyl radical monosubstituted with a substituent Y chosen from Cl, Br, I and $CF_3$, or a phenyl radical disubstituted with a substituent Y and a substituent Z, Y and Z, which may be identical or different, being each chosen from Cl, Br, I and $CF_3$, or forming together a saturated or unsaturated or aromatic, optionally substituted, ring which may contain one or more heteroatoms, in particular a ring comprising 5 to 8 atoms, preferably comprising 6 atoms,
or R represents a radical:

where $R^4$ represents a linear or branched, saturated or unsaturated, hydrocarbon-based radical,
and $R^5$ represents a linear or branched, saturated or unsaturated, hydrocarbon-based radical, optionally substituted, a $COR^6$ group or a $CO_2R^6$ group, where $R^6$ represents a hydrogen atom or a linear or branched, saturated or unsaturated, hydrocarbon-based radical.

Any isomer form of these compounds on the $C_{2'}$ carbon ($2'\alpha$ and $2'\beta$ stereoisomers) and any mixture of such isomer forms also fall within the scope of the invention. Starting from a mixture of isomers, each isomer can be obtained by methods which are conventional in themselves for those skilled in the art.

Furthermore, in formula (I) above, $R^4$ and $R^5$ are interchangeable.

In the present description, the term "monosubstituted phenyl radical" is intended to mean a phenyl radical substituted with one substituent or more, i.e. a phenyl radical substituted with at least one substituent Y. Likewise, the term "disubstituted phenyl radical" is intended to mean a phenyl radical substituted with two substituents or more, i.e. a phenyl radical substituted with at least one substituent Y and one substituent Z.

It has been discovered by the inventors that these particular compounds which are analogs of strigolactones as regards the ring D, and which are novel compounds, are particularly active for repressing plant branching. Their effectiveness, which is much greater than that of natural strigolactones, is comparable to that of the other synthetic analog compounds proposed by the prior art, in particular GR24 and GR5.

In particular, the present inventors have discovered that the strigolactone analogs corresponding to formula (I) are capable of inhibiting the sprouting of axillary buds, in particular in pea (*Pisum sativum* L.), at a concentration below that of natural strigolactones.

The compounds according to the invention are also particularly easy to prepare, in particular in comparison with the 4-rings strigolactone analogs. They also advantageously exhibit a stability in aqueous medium which is much higher than that of natural strigolactones, which are inherently unstable in water, in particular at pH above 7, but also than that of GR24 and GR5. Their cytotoxicity is also advantageously much lower than that of these synthetic compounds GR24 and GR5.

Particularly advantageously, the compounds according to the invention also act only weakly on the germination of the seeds of parasitic plants, in particular of the *orobanche* type. In particular, they have an activity which is at least 10 to 100 000 times lower than the GR24 and GR5 compounds with respect to the germination of seeds of branching broomrapes (*Phelipanche ramosa, Orobanche minor* and *Orobanche cumana*) and of *Striga hermonthica*. Since the pullulation of such harmful parasitic plants is proving to be an increasingly present problem in both temperate regions and tropical regions, the advantage of having means for treating plant crops which do not promote the germination of the seeds of these parasitic plants, contrary to natural strigolactones or to most of their synthetic analogs described by the prior art, which, for their part, induce said germination, is easily understood.

According to one preferred characteristic of the compounds according to the invention, $R^3$ represents a linear $C_1$-$C_{10}$ alkyl radical, preferably a methyl radical.

$R^1$ and $R^2$ also each preferably represent a hydrogen atom or a linear or branched $C_1$-$C_{10}$ alkyl radical.

More preferably, $R^1$ represents a hydrogen atom and $R^2$ represents a linear or branched $C_1$-$C_{10}$ alkyl radical, preferably a methyl radical.

Preferentially, X represents a sulfur atom.

In particular embodiments of the invention, R represents a phenyl radical substituted at least in the para-position.

A compound which is particularly preferred according to the invention corresponds to general formula (II):

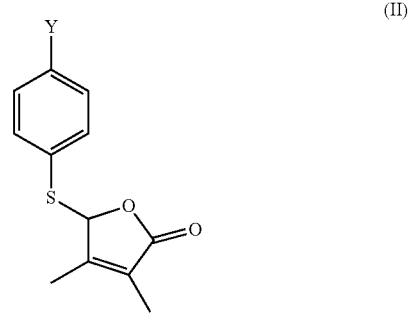

(II)

in which Y is chosen from Cl, Br, I and $CF_3$, and in which X is a sulfur atom, $R^1$ is a hydrogen atom, $R^2$ and $R^3$ are both methyl radicals, and R is a phenyl radical monosubstituted with the substituent Y in the para-position.

Among the compounds corresponding to general formula (II) above, mention may in particular be made of the compound in which Y is a chlorine atom, corresponding to general formula (IIa) below, the compound in which Y is a bromine atom, corresponding to general formula (IIb) below, and the compound in which Y represents CF$_3$, corresponding to formula (IIc) below:

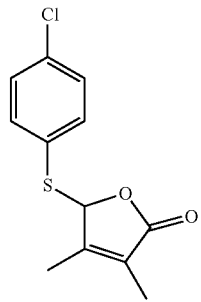
(IIa)

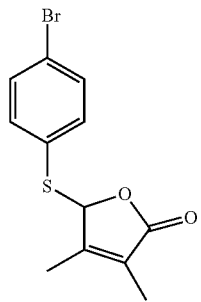
(IIb)

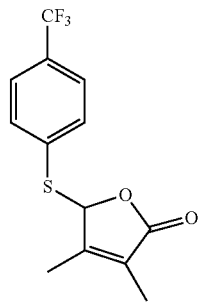
(IIc)

Another compound according to the invention corresponds to general formula (II'):

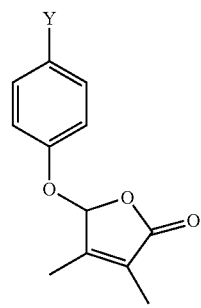
(II')

in which Y is chosen from Cl, Br, I and CF$_3$, and in which X is an oxygen atom, R$^1$ is a hydrogen atom, R$^2$ and R$^3$ are both methyl radicals, and R is a phenyl radical monosubstituted with the substituent Y in the para-position.

Other particular compounds according to the invention are such that R represents a disubstituted phenyl radical of coumarin type, of formula:

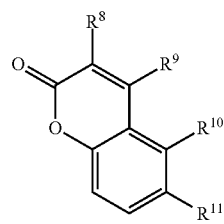

in which R$^8$, R$^9$, R$^{10}$ and R$^{11}$, which may be identical or different, each represent a hydrogen atom, Cl, Br, I, CF$_3$, CHO, CN, NO$_2$, a linear or branched, saturated or unsaturated, optionally substituted, hydrocarbon-based radical, or a CO$_2$R$^{12}$ group, where R$^{12}$ represents a hydrogen atom or a linear or branched, saturated or unsaturated, preferably C$_1$-C$_{10}$, hydrocarbon-based radical.

Such compounds thus correspond to general formula (II") below:

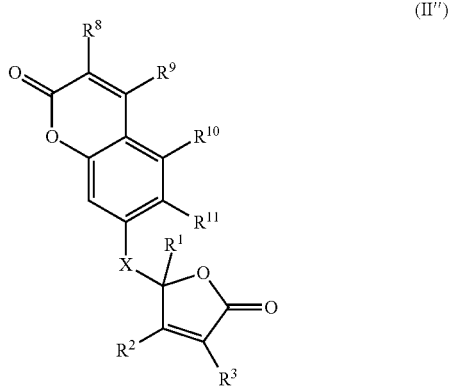
(II")

in which:

X represents an oxygen atom, a sulfur atom, NH or an N-alkyl radical,

R$^1$ and R$^2$, which may be identical or different, each represent a hydrogen atom or a linear or branched, saturated or unsaturated, C$_1$-C$_{10}$, hydrocarbon-based radical, R$^1$ and R$^2$ not both representing a hydrogen atom, R$^3$ represents a linear or branched, saturated or unsaturated, C$_1$-C$_{10}$, hydrocarbon-based radical, R$^8$, R$^9$, R$^{10}$ and R$^{11}$ are as defined above.

More particularly, advantageous compounds according to the invention correspond to general formula (II'''):

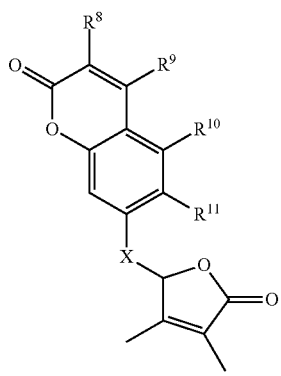

(II''')

in which X, $R^8$, $R^9$, $R^{10}$ and $R^{11}$ are as defined above.

One particular compound according to the invention is such that $R^8$, $R^9$, $R^{10}$ and $R^{11}$ all each represent a hydrogen atom.

In different embodiments of the invention, R represents a radical:

where $R^4$ represents a linear or branched $C_1$-$C_{15}$ alkyl radical or alkenyl radical, and $R^5$ represents a linear or branched, saturated or unsaturated, $C_1$-$C_{10}$, preferably $C_1$-$C_5$, optionally substituted, hydrocarbon-based radical, a $COR^6$ group or a $CO_2R^6$ group, where $R^6$ represents a linear or branched, $C_1$-$C_{10}$, preferably $C_1$-$C_5$, hydrocarbon-based radical.

The compounds of general formula (III):

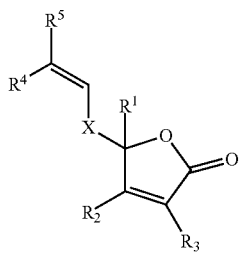

(III)

in which $R^1$, $R^2$, $R^3$, $R^4$ and $R^5$ are as defined above, thus fall within the scope of the invention.

Particular compounds according to the invention correspond to general formula (III) above, in which $R^4$ represents a linear or branched, preferably $C_1$-$C_{15}$, alkyl radical or alkenyl radical, and $R^5$ represents a linear or branched, preferably unsaturated, $C_1$-$C_{10}$, preferably $C_1$-$C_5$, hydrocarbon-based radical which is substituted, preferentially at its free end, with an electron-withdrawing group. Examples of such electron-withdrawing groups are CHO, CN, $NO_2$ and $CO_2R^7$, where $R^7$ represents a linear or branched, $C_1$-$C_{10}$, preferably $C_1$-$C_5$, hydrocarbon-based radical.

The compounds of formula (III) above, in which $R^3$ represents a methyl radical, prove to be particularly advantageous from the point of view of the effectiveness of inhibition of the sprouting of axillary buds. Furthermore, advantageously, $R^1$ represents a hydrogen atom and/or $R^2$ also represents a methyl radical.

Compounds corresponding to general formula (III') below thus prove to be particularly advantageous:

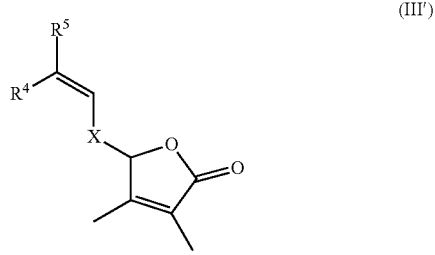

(III')

and more particularly the compounds of general formula (III") below:

(III")

in which EWG represents an electro-withdrawing group chosen from CHO, CN, $NO_2$ and $CO_2R^7$, where $R^7$ represents a linear or branched, $C_1$-$C_{10}$, preferably $C_1$-$C_5$, hydrocarbon-based radical, and X represents O, NH or S.

The compounds according to the invention can be obtained by any appropriate synthesis route. Those skilled in the art will be able to determine the steps, the operating conditions and the precursors to use according to the particular structure of the compound of general formula (I) targeted.

A process for synthesizing the compounds according to the invention corresponding to general formula (II), (II') or (III') above can correspond to the following general reaction scheme:

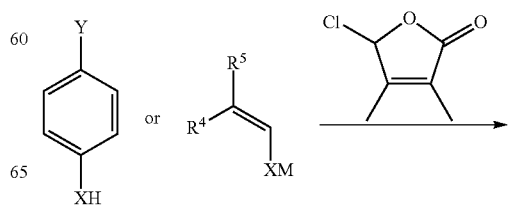

-continued

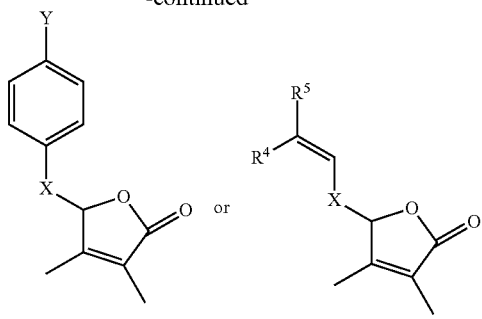

in which M represents an alkali metal, for example a sodium or potassium atom.

Any other mode of synthesis that those skilled in the art will be able to identify from their general knowledge also falls within the scope of the invention.

Another aspect of the invention is a composition comprising a compound as defined above, which can be used in particular for the treatment of higher plants with a view to controlling their growth and their architecture, more particularly their branching.

Preferentially, the concentration of said compound in said composition is between 0.1 nM and 10 µM, preferentially between 0.1 and 1000 nM, more preferentially between 1 and 100 nM.

A third aspect of the invention is the use of a compound as defined above, and/or of a composition comprising same, for the treatment of a higher plant with a view to controlling its growth and its architecture.

More particularly, an appropriate amount of a compound in accordance with the invention is brought into contact with the plant so as to inhibit the formation of at least one branch.

The term "inhibit" is intended to mean, in the present description, permanently or temporarily repress the growth of a bud. Thus, according to the invention, it is possible to suppress a branching by permanently inhibiting the growth of the corresponding bud, or to render said bud dormant so as to delay its growth over time.

The term "branch" is intended to mean the outgrowth from the axillary bud located at the leaf axil, whether it is a branch, a flower or an inflorescence.

The inhibition may be overall, i.e. affect all the axillary buds at the time of the treatment of the plant, or targeted, i.e. affect only buds specifically targeted by the treatment.

The treated plants can be cultivated both in greenhouses and in fields, in vitro or even soilless.

An appropriate amount is understood to mean an amount which is at least sufficient to act on the growth and the architecture of the plant to be treated. This amount is evaluated for each particular case, depending in particular on the nature of the plant to be treated and on the desired degree of control of the branching, for example depending on whether it is desired to permanently or temporarily inhibit the growth of the bud.

According to the invention, a composition comprising a compound in accordance with the invention can be applied to an at least partial portion of the aerial part of the plant. For example, it is possible to apply, by spraying or by depositing, said composition on axillary buds of the plant that it is desired to repress, so as to control the growth of the buds thus treated, or more generally on the part of the plant of which it is desired to control the growth. It is otherwise possible to inject the composition comprising a compound in accordance with the invention into an aerial part of said plant, for example in the buds themselves, or the stems bearing the buds to be repressed, so as to control the growth of the plant located above the injection zone.

In another embodiment, the invention provides for introducing a composition comprising the compound in accordance with the invention via at least one root of said plant, so as to control the branching and/or the height of the plant. This can be carried out via an enrichment of the soil with compound according to the invention so as to nonselectively reduce the number of stems or to check their growth. Indeed, the inventors have observed that the branch growth SMS repression signal migrates in the root-stem direction, which implies that it is carried by the crude sap of the xylem.

Advantageously, the concentration of compound in accordance with the invention in the composition is at least 0.1 nM and will vary depending on whether it is desired to permanently or temporarily inhibit the growth of the bud, the concentration also depending on the nature of the plant to be treated. Generally, the concentration of the compound in the composition will vary between 0.1 nM and 10 µM, preferentially between 0.1 and 1000 nM, more preferentially between 1 and 100 nM.

Likewise, the number of days of treatment can vary according to the plant, to its age at the time of treatment, to the desired permanent or non-permanent effect, etc.

BRIEF DESCRIPTION OF THE DRAWINGS

The characteristics and advantages of the process according to the invention will become more clearly apparent in the light of the implementation examples below, which are provided simply by way of illustration and are no way limiting with respect to the invention, with the support of FIGS. 1 to 17, in which.

DETAILED DESCRIPTION OF THE EMBODIMENTS

Example 1

Figure 1:
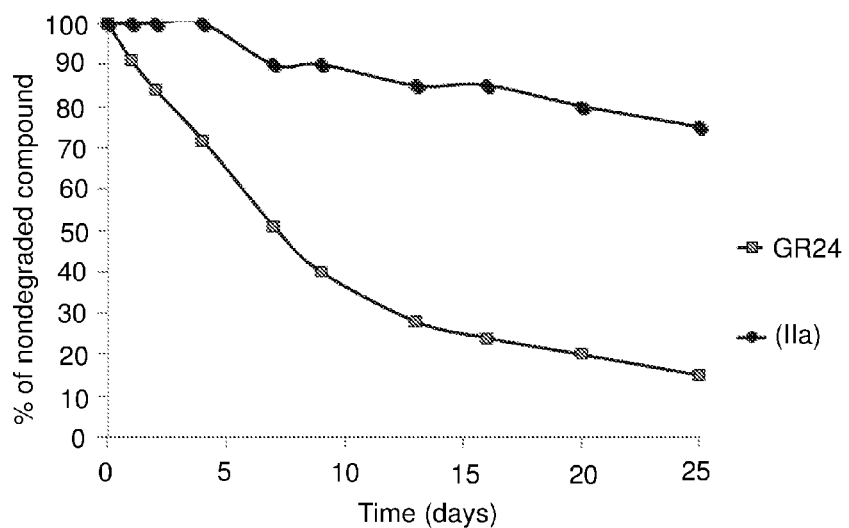
FIG. 1 is a curve showing the results of an analysis of chemical stability in aqueous solution (50 µg/ml of compound in methanol/water: 1/4, pH 6.7, 21° C.), for the compound (IIa) in accordance with the invention and the comparative compound GR24, the % of nondegraded compound in the solution being represented as a function of time.

Synthesis of Examples of Compounds According to the Invention and of Examples of Comparative Compounds 1/ Materials and Methods The infrared spectra were recorded in a film on a diamond window. The data are given in cm$^{-1}$ (v, cm$^{-1}$).

The $^1$H and $^{13}$C NMR spectra were recorded on solutions in CDCl$_3$, using the protic solvent CHCl$_3$ ($\delta_H$=7.24 ppm) or CDCl$_3$ ($\delta_C$=77.23 ppm) as internal reference and are given in ppm.

The mass spectra were determined by electrospray ionization (ESI).

All the reactions were monitored by thin layer chromatography (TLC) on 0.2 mm aluminum plates precoated with silica gel, using UV light and an ethanolic solution containing 5% of phosphomolybdic acid, and heat as developing agent.

Flash chromatography was carried out on silica gel 60, 40-63 µm (400-230 mesh), with ethyl acetate (EtOAc) and heptane as eluents.

The commercially available reagents and solvents were purified and dried when necessary using conventional methods.

Dimethylformamide DMF and dichloromethane CH$_2$Cl$_2$ were dried by distillation over calcium hydride, acetate was dried by distillation over anhydrous CaSO$_4$.

Unless otherwise indicated, all the other reagents were obtained from commercial sources and used without further purification.

2/ Compound (IIa)

The compound corresponding to formula (IIa), 5-((4-chlorophenyl)thio)-3,4-dimethylfuran-2(5H)-one:

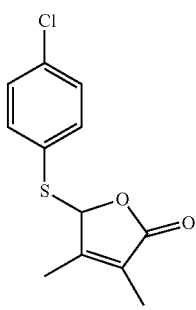

(IIa)

was synthesized from 4-chlorothiophenol and from 5-chloro-3,4-dimethylfuran-2(5H)-one, according to the following reaction scheme:

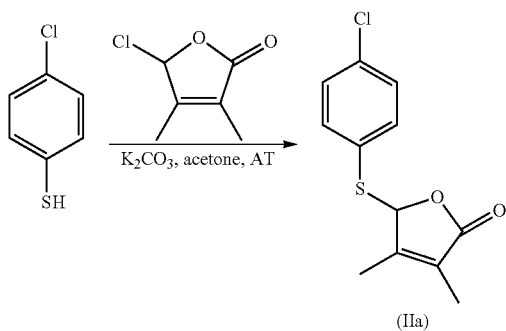

(IIa)

in the following way.

A solution of 5-chloro-3,4-dimethylfuran-2(5H)-one (405 mg, 2.6 mmol) (prepared according to the method of Canevet et al., 1978) in anhydrous acetone (5 ml) is added to a solution of commercial 4-chlorothiophenol (400 mg, 2.76 mmol) in anhydrous acetone (10 ml) with anhydrous $K_2CO_3$ (459 mg, 3.31 mmol), placed at ambient temperature under argon. The progression of the reaction is monitored by TLC ($SiO_2$; 8:2 heptane/EtOAc).

After stirring for 1 day, the acetone is evaporated off. The crude is purified by silica chromatography (eluent 8:2 heptane/EtOAc) to give the compound (IIa) in the form of a white solid (361 mg, 1.42 mmol, 51%).

Mp: 74.5-76.9° C.

$^1$H NMR (300 MHz, CDCl$_3$): δ 7.34 (dt, J=8.7, 2.1 Hz, 2H), 7.20 (dt, J=8.7, 2.1 Hz, 2H), 5.83-5.82 (m, 1H), 1.96 (t, J=1.0 Hz, 3H), 1.64 (t, J=1.0 Hz, 3H).

$^{13}$C NMR (75 MHz, CDCl$_3$): δ 172.6 (C), 155.2 (C), 135.4 (C), 135.2 (2CH), 129.2 (2CH), 128.2 (C), 126.2 (C), 88.1 (CH), 12.6 (CH$_3$), 8.5 (CH$_3$).

IR $\nu_{max}$ (film): 2924, 1758, 1673, 1476, 1093, 985 cm$^{-1}$.

HRMS (ESI): m/z calculated for $C_{12}H_{12}ClO_2S$ [M+H]$^+$: 255.0247. found: 255.0245.

3/ Compound (IIb)

The compound corresponding to formula (IIb), 5-((4-chlorophenyl)thio)-3,4-dimethylfuran-2(5H)-one:

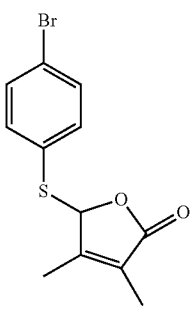

(IIb)

was synthesized from 4-bromothiophenol and from 5-chloro-3,4-dimethylfuran-2(5H)-one, according to a reaction scheme similar to that indicated above for the compound (IIa), in the following way.

A solution of 5-chloro-3,4-dimethylfuran-2(5H)-one (263.8 mg, 1.8 mmol) in anhydrous acetone (10 ml) is added to a solution of commercial 4-bromothiophenol (283.6 mg, 1.5 mmol) in anhydrous acetone (15 ml) with anhydrous $K_2CO_3$ (337 mg, 3 mmol, 3 eq.), placed at ambient temperature under argon. The progression of the reaction is monitored by TLC ($SiO_2$; 8:2 heptane/EtOAc).

After stirring for 8 days, the acetone is evaporated off and the residue is taken up with $CH_2Cl_2$ so as to be filtered through celite. After evaporation, the resulting brown solid is purified by silica chromatography (introduction and elution with $CH_2Cl_2$, silica column 2 cm in diameter and 45 cm in height) to give the compound (IIb) in the form of a transparent solid (152.4 mg, 0.51 mmol, 34% yield).

Mp: 91° C.

$^1$H NMR (CDCl$_3$, 500 MHz): δ (ppm) 1.71 (broad s, 3H), 2.03 (broad s, 3H), 5.89 (broad s, 1H), 7.38 (d, J=8.2 Hz, 2H), 7.46 (d, J=8.2 Hz, 2H).

$^{13}$C NMR (CDCl$_3$, 125.5 MHz): δ (ppm) 8.7 (CH$_3$), 12.8 (CH$_3$), 88.2 (CH), 123.8 (C), 126.6 (C), 129.0 (C), 132.4 (2CH), 135.5 (2CH), 155.1 (C), 172.7 (C).

IR $\nu_{max}$ (film): 1760, 1686, 1673 cm$^{-1}$.

MS (ES$^-$): m/z (%) 297.0 (99%, [M–H]$^-$).

HRMS (ESI): m/z calculated for $C_{12}H_{10}O_2SBr$ [M–H]$^-$: 296.9585. found: 296.9592.

4/ Compound (IIc)

The compound corresponding to formula (IIc), 3,4-dimethyl-5-((4-(trifluoromethyl)phenyl)thio)furan-2(5H)-one:

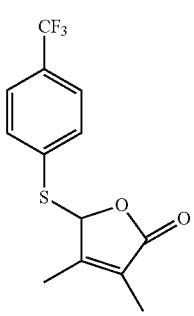

(IIc)

was synthesized from 4-(trifluoromethyl)thiophenol and 5-chloro-3,4-dimethylfuran-2(5H)-one, according to a reaction scheme similar to that indicated above for the compound (IIa), in the following way.

A solution of 5-chloro-3,4-dimethylfuran-2(5H)-one (263.8 mg, 1.8 mmol) in anhydrous acetone (10 ml) is added to a solution of commercial 4-(trifluoromethyl)thiophenol (267.3 mg, 1.5 mmol) in anhydrous acetone (15 ml) with anhydrous $K_2CO_3$ (337 mg, 3 mmol, 3 eq.), placed at ambient temperature under argon. The progression of the reaction is monitored by TLC ($SiO_2$; 8:2 heptane/EtOAc).

After stirring for 8 days, the acetone is evaporated off and the residue is taken up with $CH_2Cl_2$ so as to be filtered through celite. After evaporation, the resulting brown oil is purified twice by silica chromatography (introduction and elution with $CH_2Cl_2$, silica column 2 cm in diameter and 45 cm in height) to give the compound (IIc) in the form of a transparent pale yellow oil (112.8 mg, 0.39 mmol, 26% yield).

$^1$H NMR (CDCl$_3$, 500 MHz): δ (ppm) 1.75 (broad s, 3H), 2.06 (broad s, 3H), 5.99 (broad s, 1H), 7.57 (d, J=8.6 Hz, 2H), 7.63 (d, J=8.6 Hz, 2H).

$^{13}$C NMR (CDCl$_3$, 125.5 MHz): δ (ppm) 8.7 (CH$_3$), 12.8 (CH$_3$), 88.0 (CH), 122.1 (C), 125.7 (CF$_3$), 126.0 (CH), 126.1 (CH), 126.8 (CH), 132.8 (2CH), 135.9 (C), 154.8 (C), 172.6 (C).

IR $ν_{max}$ (film): 1766, 1687, 1672 cm$^{-1}$.

MS (ES$^-$): m/z (%) 287.0 (100%, [M−H]$^-$)

HRMS (ESI): m/z calculated for $C_{13}H_{10}O_2F_3S$ [M−H]$^-$: 287.0354. found: 287.0342.

5/ Compound (II'd)

The compound corresponding to formula (II'd), 5-(4-chlorophenoxy)-3,4-dimethylfuran-2(5H)-one:

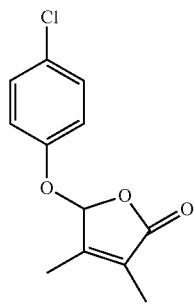

(II'd)

was synthesized from 4-chlorophenol and 5-chloro-3,4-dimethylfuran-2(5H)-one, according to a reaction scheme similar to that indicated above for the compound (IIa), in the following way.

A solution of 5-chloro-3,4-dimethylfuran-2(5H)-one (1.45 g, 9.89 mmol) (prepared according to the method of Canevet et al., 1978) in anhydrous acetone (20 ml) was added to a solution of commercial 4-chlorophenol (0.847 g, 6.59 mmol) in anhydrous acetone (50 ml) with anhydrous $K_2CO_3$ (1.821 g, 13.13 mmol), placed at ambient temperature under argon. The progression of the reaction is monitored by TLC ($SiO_2$; 8:2 heptane/EtOAc).

After stirring for 2 days, the acetone is evaporated off. The crude is purified by silica chromatography (eluent 8:2 heptane/EtOAc) then recrystallized (hexane/EtOAc) to give the compound (II'd) in the form of a white solid (793 mg, 3.33 mmol, 50%).

Mp: 84-85° C.

$^1$H NMR (300 MHz, CDCl$_3$): δ 7.27 (dt, J=9.0, 3.2 Hz, 2H), 7.06 (dt, J=9.0, 3.0 Hz, 2H), 6.00-5.99 (broad s, 1H), 2.05 (t, J=1.0 Hz, 3H), 1.87 (t, J=1.0 Hz, 3H).

$^{13}$C NMR (75 MHz, CDCl$_3$): δ 171.8 (C), 155.5 (C), 153.6 (C), 129.8 (2CH), 128.9 (C), 127.4 (C), 118.5 (2CH), 100.9 (CH), 11.8 (CH$_3$), 8.7 (CH$_3$).

IR $ν_{max}$ (film): 1773, 1694, 1490, 1227, 974 cm$^{-1}$.

MS (ES$^-$): m/z (%) 237.0 (100%, [M−H]$^-$), 273.0 (90%, [M+Cl]$^-$).

HRMS (ESI): m/z calculated for $C_{12}H_{10}ClO_3$ [M−H]$^-$: 237.0318. found: 237.0325.

6/ Compound (II'e)

The compound corresponding to formula (II'e), 5-(4-bromophenoxy)-3,4-dimethylfuran-2(5H)-one:

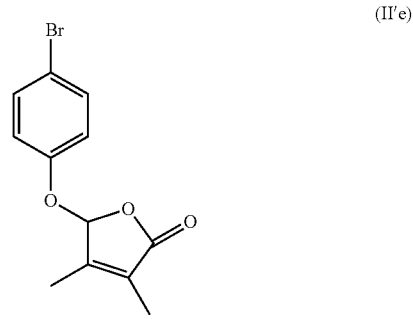 [SMILES: CC1=C(C)C(Oc2ccc(C(F)(F)F)cc2)OC1=O]

(II'e)

was synthesized from 4-bromophenol and 5-chloro-3,4-dimethylfuran-2(5H)-one, according to a reaction scheme similar to that indicated above for the compound (IIa), in the following way.

A solution of 5-chloro-3,4-dimethylfuran-2(5H)-one (245.0 mg, 1.67 mmol) in anhydrous acetone (10 ml) is added to a solution of commercial 4-bromophenol (259.5 mg, 1.5 mmol) in anhydrous acetone (15 ml) with anhydrous $K_2CO_3$ (337 mg, 3 mmol, 3 eq.), placed at ambient temperature under argon. The progression of the reaction is monitored by TLC ($SiO_2$; 8:2 heptane/EtOAc).

After stirring for 17 days, the acetone is evaporated off and the residue is taken up with $CH_2Cl_2$ so as to be filtered through celite. After evaporation, the resulting brown solid is purified by silica chromatography (introduction and elution with $CH_2Cl_2$, silica column 2 cm in diameter and 45 cm in height) to give the compound (II'e) in the form of a transparent solid (241.7 mg, 0.85 mmol, 57% yield).

Mp: 94° C.

$^1$H NMR (CDCl$_3$, 500 MHz): δ (ppm) 1.89 (broad s, 3H), 2.07 (broad s, 3H), 6.02 (broad s, 1H), 7.03 (d, J=9.0 Hz, 2H), 7.43 (d, J=9.0 Hz, 2H).

$^{13}$C NMR (CDCl$_3$, 125.5 MHz): δ (ppm) 8.7 (CH$_3$), 11.7 (CH$_3$), 100.8 (CH), 116.3 (C), 118.9 (2CH), 127.3 (C), 132.8 (2CH), 153.5 (C), 156.0 (C), 171.7 (C).

IR (film): ν (cm$^{-1}$) 1772, 1693, 1582.

MS (ES$^-$): m/z (%) 281.0 (99%, [M−H]$^-$).

HRMS: m/z (280.9809, [M−H]$^-$; calculated for $C_{12}H_{10}O_3Br$: 280.9813.

7/ Compound (II'f)

The compound corresponding to formula (II'f), 3,4-dimethyl-5-(4-(trifluoromethyl)phenoxy)furan-2(5H)-one:

(II'f)

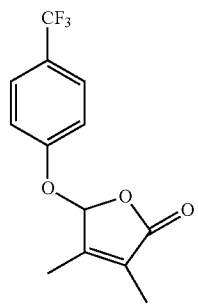

was synthesized from 4-(trifluoromethyl)phenol and 5-chloro-3,4-dimethylfuran-2(5H)-one, according to a reaction scheme similar to that indicated above for the compound (IIa), in the following way.

A solution of 5-chloro-3,4-dimethylfuran-2(5H)-one (263.4 mg, 1.8 mmol) in anhydrous acetone (10 ml) is added to a solution of commercial 4-(trifluoromethyl)phenol (243.2 mg, 1.5 mmol) in anhydrous acetone (15 ml) with anhydrous $K_2CO_3$ (337 mg, 3 mmol, 3 eq.), placed at ambient temperature under argon. The progression of the reaction is monitored by TLC ($SiO_2$; 8:2 heptane/EtOAc).

After stirring for 8 days, the acetone is evaporated off and the residue is taken up with $CH_2Cl_2$ so as to be filtered through celite. After evaporation, the resulting brown solid is purified by silica chromatography (introduction and elution with $CH_2Cl_2$, silica column 2 cm in diameter and 45 cm in height) to give the compound (II'f) (132.2 mg, 32%) in the form of a transparent solid.

Mp: 97° C.

$^1$H NMR (CDCl$_3$, 500 MHz): δ (ppm) 1.91 (broad s, 3H), 2.09 (broad s, 3H), 6.12 (broad s, 1H), 7.22 (d, J=8.6 Hz, 2H), 7.61 (d, J=8.6 Hz, 2H).

$^{13}$C NMR (CDCl$_3$, 125.5 MHz): δ (ppm) 8.7 (CH$_3$), 11.7 (CH$_3$), 100.1 (CH), 116.9 (2CH), 122.4 (C), 126.0 (CF$_3$), 127.3 (2CH), 127.4 (C), 153.4 (C), 159.2 (C), 171.6 (C).

IR (film): ν (cm$^{-1}$) 1768, 1697, 1614.

MS (ES$^-$): m/z (%) 271.1 (100%, [M−H]$^-$).

HRMS: m/z (271.0579, [M−H]$^-$); calculated for C$_{13}$H$_{10}$O$_3$F$_3$: 271.0582.

8/ Compound (II"g)

The compound corresponding to formula (II"g), 7-[3,4-dimethylfuran-2(5H)-one]oxycoumarin:

(II"g)

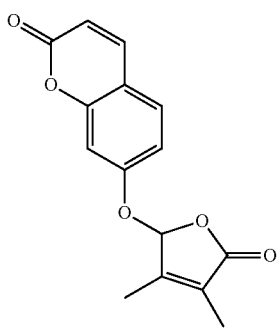

was synthesized from 7-hydroxycoumarin and 5-chloro-3,4-dimethylfuran-2(5H)-one, according to the following reaction scheme:

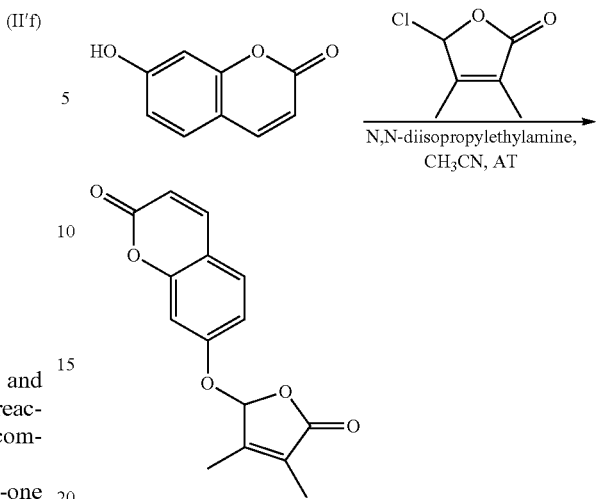

in the following way.

Solid 7-hydroxycoumarin, which is commercially available or readily accessible according to the method of Timonen et al. (2011) (CAS RN: 93-35-6, 300 mg, 1.85 mmol), is added to a solution of 5-chloro-3,4-dimethylfuran-2(5H)-one (352 mg, 2 mmol) (prepared according to the method of Cavenet et al. (1978)) in anhydrous acetonitrile (10 ml), placed at ambient temperature under argon. N,N-Diisopropylethylamine is then added (697 μl, 4 mmol). The progression of the reaction is monitored by TLC ($SiO_2$; 1:1 heptane/EtOAc).

After stirring for 12 h, the acetonitrile is evaporated off. The crude is purified by silica chromatography (eluent 6:4 heptane/EtOAc) to give the compound (II"g) in the form of a white solid (423 mg, 1.55 mmol, yield: 84%).

Mp: 176.2° C.

$^1$H NMR (300 MHz, CDCl$_3$): δ 1.85 (t, J=1.2 Hz, 3H), 2.04 (t, J=0.9 Hz, 3H), 6.08 (s, 1H), 6.24-6.27 (d, J=9.5 Hz, 1H), 6.98-7.01 (m, 2H), 7.37-7.39 (d, J=8.1 Hz, 1H), 7.58-7.61 (d, J=9.6 Hz, 1H).

$^{13}$C NMR (75 MHz, CDCl$_3$): δ 8.7 (CH$_3$), 11.7 (CH$_3$), 99.9 (CH), 104.6 (CH), 113.5 (CH), 114.8 (CH), 114.9 (CH), 127.5 (C), 129.3 (CH), 143.1 (CH), 153.3 (C), 155.5 (C), 159.5 (C), 160.7 (C), 171.4 (C).

IR ν$_{max}$ (film): 661, 750, 834, 886, 975, 1052, 1088, 1131, 1162, 1195, 1236, 1285, 1318, 1361, 1387, 1505, 1565, 1615, 1624, 1689, 1745, 1781, 3081 cm$^{-1}$.

HRMS (ESI): m/z calculated for C$_{15}$H$_{13}$O$_5$ [M+H]$^+$: 273.0718. found: 273.0753.

9/ Compound (IIIa)

The compound corresponding to formula (IIIa), 3-((3,4-dimethyl-5-oxo-2,5-dihydrofuran-2-yl)oxy)-2-methylacrylaldehyde:

(IIIa)

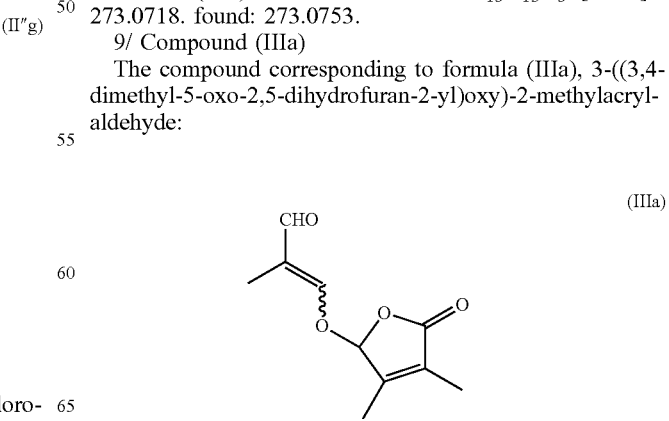

was synthesized from the sodium salt of methylmalondialdehyde and 5-chloro-3,4-dimethylfuran-2(5H)-one, according to the reaction scheme below:

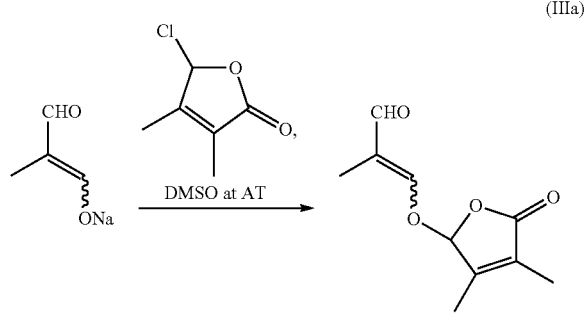

For this, the sodium salt of methylmalondialdehyde (obtained in accordance with the publication by Nair et al., 1981) (244 mg, 2.6 mmol), 5-chloro-3,4-dimethylfuran-2(5H)-one (165 mg, 1.13 mmol) and dimethyl sulfoxide (2 ml) are mixed and stirred at ambient temperature for 14 h. The completion of the reaction is verified by TLC (heptane/EtOAc, 8/2 v/v). Water is then added to the mixture until complete dissolution of the salts, then the aqueous phase is extracted 3 times with dichloromethane. The combined organic phases are dried with $Na_2SO_4$, filtered and evaporated under reduced pressure until a dry residue is obtained.

The crude product is purified by silica gel chromatography with a linear gradient of 0-50% v/v of EtOAc in heptane, so as to obtain the desired compound (IIIa) (202 mg, 1.03 mmol, yield 91%) in the form of a white solid.

Rf=0.13 (heptane/EtOAc, 8/2 v/v)

$^1$H NMR (500 MHz, $CDCl_3$): δ: 9.36 (s, 1H), 7.18 (s, 1H), 6.01 (s, 1H), 2.08 (s, 3H), 1.94 (s, 3H), 1.73 (s, 3H).

$^{13}$C NMR (125 MHz, $CDCl_3$) δ: 191.5 (CH), 170.9 (C), 161.4 (CH), 152.6 (C), 128.2 (C) 123.3 (C), 101.8 (CH), 11.4 ($CH_3$), 8.8 ($CH_3$), 6.6 ($CH_3$)

IR $v_{max}$ (film): 1771, 1684, 1652, 1168, 978 $cm^{-1}$.

MS (ESI): m/z=197 ($MH^+$, 100%).

HRMS (ESI, positive mode): calculated for $C_{10}H_{13}O_4$ [M+H$^+$]: 197.0814. Found: 197.0809.

10/ Compound (IIIb)

The compound corresponding to formula (IIIb), 5-((3,4-dimethyl-5-oxo-2,5-dihydrofuran-2-yl)oxy)-4-methylpenta-2,4-dienoate:

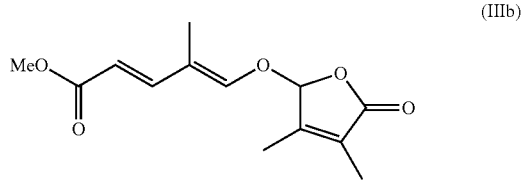 [SMILES: COC(=O)/C=C/C(C)=C/OC1OC(=O)C(C)=C1C]

is synthesized from the compound (IIIa) above, according to the reaction scheme below:

The compound (IIIa) (100 mg, 0.5 mmol) is dissolved in dry toluene (10 ml). Commercially available methyl (triphenylphosphoranylidene)acetate (203 mg, 0.61 mmol) is added and the resulting mixture is stirred at reflux for 12 h. The completion of the reaction is verified by TLC (heptane/EtOAc, 7:3, v/v). The reaction mixture is then concentrated under reduced pressure and the residue is purified by chromatography on a column of silica gel with a linear gradient of EtOAc (0-20%) in heptane as mobile phase, so as to obtain the desired dienoate (IIIb) in the form of a white powder (77 mg, 305 μmol, yield=80% after elimination of the unreacted starting aldehyde (IIIa)).

$^1$H NMR (500 MHz, $CDCl_3$) δ: 7.23 (d, J=15.4 Hz, 1H), 6.69 (s, 1H), 5.85 (s, 1H), 5.79 (d, J=15.4 Hz, 1H), 3.72 (s, 3H), 1.99 (s, 3H), 1.87 (s, 3H), 1.73 (s, 3H).

$^{13}$C NMR (125 MHz, $CDCl_3$) δ: 171.2, 167.7, 153.0, 148.3, 144.9, 127.8, 117.4, 115.1, 101.6, 51.5, 11.4, 9.4, 8.6.

IR $v_{max}$ (film, $cm^{-1}$): 1767, 1718, 1639, 1317, 1154, 979.

HRMS (ESI, positive mode): m/z=253.1076 [M+H], calculated for $C_{13}H_{17}O_5$=253.1031.

11/ Compound (IIIc)

The compound corresponding to formula (IIIc), (E)-3,4-dimethyl-5-((2-methylbuta-1,3-dien-1-yl)oxy)furan-2(5H)-one:

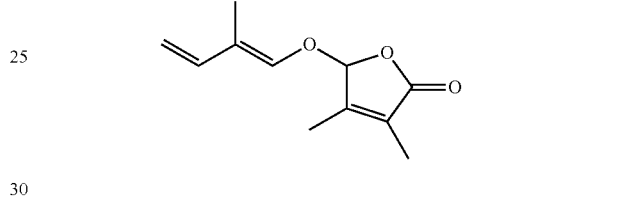

is synthesized from the compound (IIIa) above, according to the reaction scheme below:

Methyltriphenylphosphonium bromide (1.25 g, 3.5 mmol) is dissolved in dry THF (4 ml) and cooled to −50° C. Butyllithium (2.25 ml, 3.6 mmol, 1.6 M in hexane) is added dropwise and the resulting mixture is heated to −10° C. over the course of 45 min, and cooled to −78° C. A solution of (IIIa) (400 mg, 2.04 mmol) in THF (4 ml) is added dropwise and the mixture is stirred for 2 h 30 at −50° C. The reaction mixture is then left to heat back up to −20° C. before being poured into a mixture of $CH_2Cl_2$ and phosphate buffer (pH 7) (v/v; 1/1). The mixture is extracted 3 times with $CH_2Cl_2$, the combined organic phases are washed with water and dried under reduced pressure, and the resulting residue is purified by chromatography on a column of silica gel with a linear gradient of EtOAc (0-50%) in heptane as mobile phase, so as to obtain the desired diene (IIIc) in the form of a pale yellow oil (150 mg, 773 μmol, yield=38%).

$^1$H NMR (500 MHz, $CDCl_3$) δ: 6.34 (s, 1H), 6.69 (s, 1H), 6.22 (dd, J=17.2, 10.7 Hz, 1H), 5.77 (s, 1H), 5.08 (d, J=17.2 Hz, 1H), 4.94 (d, J=10.7 Hz, 1H), 1.98 (s, 3H), 1.85 (s, 3H), 1.71 (s, 3H).

$^{13}$C NMR (125 MHz, $CDCl_3$) δ: 171.6, 154.2, 142.4, 135.5, 127.4, 119.2, 111.0, 101.8, 11.4, 9.04, 8.4.

IR $v_{max}$ (film, $cm^{-1}$): 1766, 1150, 960.

HRMS (ESI, positive mode): m/z=195.1020 [M+H]$^+$, calculated for $C_{11}H_{15}O_3$=195.1021.

12/ Comparative Compound 1—GR24

GR24 was prepared according to the method known per se described in Mangnus et al., 1992.

13/ Comparative Compound 2—GR5

GR5 was synthesized according to the method known per se described in Johnson et al., 1981.

14/ Comparative Compound 3—Comp. 3
The comparative compound Comp. 3, of general formula:

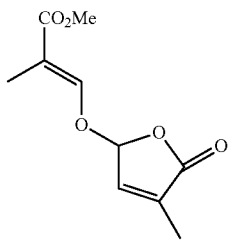

Comp. 3 which differs from the compounds according to the invention, in particular from the compounds corresponding to formula (III), in that $R^1$ and $R^2$ both represent a hydrogen atom, is prepared according to the protocol described in patent document WO 2010/137662.

15/ Comparative Compounds 4 to 6—Comp. 4, Comp. 5, Comp. 6
The comparative compounds Comp. 4, Comp. 5 and Comp. 6, of respective general formulae:

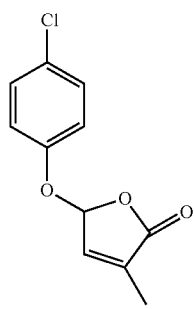

Comp. 4

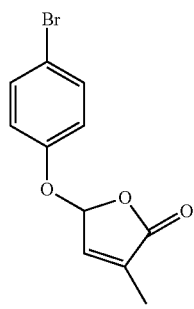

Comp. 5

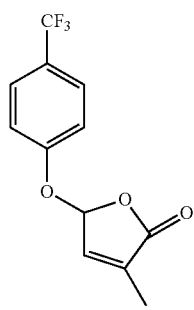

Comp. 6 which differ from the compounds according to the invention, in particular from the compounds corresponding to formula (II'), in that $R^1$ and $R^2$ both represent a hydrogen atom, are prepared according to the protocols described in patent document WO 2012/043813 and in the publication by Fukui et al. (2011).

Example 2

Studies of Stability in Aqueous Medium

1/ Compound (IIa)
The stability in aqueous medium of the compound (IIa) according to the invention and that of GR24 as comparative compound was evaluated in the following way.

Each compound was diluted in acetone (1 ml), then 50 µl of each solution were diluted with methanol (175 µl) and water (750 µl) so as to obtain a compound concentration of 50 µg/ml.

The aqueous solution thus obtained was incubated at 21° C. in HPLC vials.

Indanol (25 µl of a solution at 1 mg/ml in acetone) was added to each solution in order to serve as an internal standard.

The degradation of each compound over time was monitored by analysis of samples taken from the solution at various time intervals, by Ultra Performance Liquid Chromatograpy (UPLC) by means of an Acquity UPLC HSS $C_{18}$ column (1.8 µm, 2.1×50 mm), eluted first of all with a solution of acetonitrile at 5% in water containing 0.1% of formic acid, for 0.5 min, then with a gradient of 5% to 100% of acetonitrile in water containing 0.1% of formic acid, for 6.5 min, and with 100% of acetonitrile containing 0.1% of formic acid for 3 min. The column was maintained at a temperature of 40° C., with a flow of 0.6 ml/min.

The compounds eluted from the column were detected with a photodiode array detector.

The relative amount of nondegraded compound in the solution was determined by comparison with the internal standard.

The results obtained are shown on the curve of FIG. 1, as % of nondegraded compound in the solution as a function of incubation time.

It is clearly observed thereon that the compound (IIa) exhibits a very high chemical stability in aqueous solution, much higher than that of GR24.

2/ Compounds (IIa) and (IIIb)
In a second experiment, the stability in aqueous medium of the compounds (IIa) and (IIIb) according to the invention, and that of GR24 as comparative compound, was evaluated according to the protocol described above.

Figure 2:
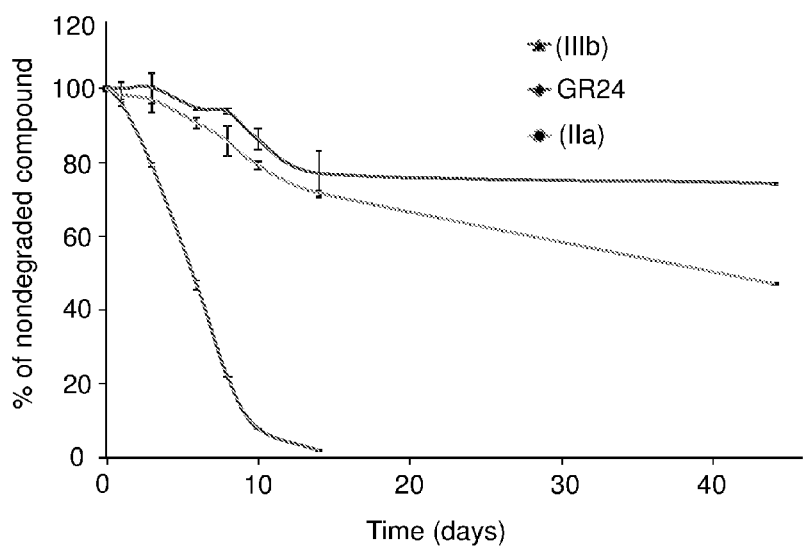
FIG. 2 is a curve showing the results of an analysis of chemical stability in aqueous solution (50 µg/ml of compound in methanol/water: 1/4, pH 6.7, 21° C.), for the respective compounds (IIa) and (IIIb) in accordance with the invention and the comparative compound GR24, the % of nondegraded compound in the solution being represented as a function of time.

The results obtained are shown in FIG. 2, as % of nondegraded compound in the solution, as a function of incubation time.

The results obtained, including over longer incubation times, confirm that the compound (IIa) exhibits a very high chemical stability in aqueous solution, much higher than that of GR24. The stability in aqueous medium of the compound (IIIb) is also even better than that of the compound (IIa).

Example 3

In Vitro Cytotoxicity Study

The cytotoxicity of the compound (IIa) according to the invention, and that of GR24 and of GR5 as comparative compounds, was evaluated in vitro, at concentrations of $10^{-4}$ M and $10^{-5}$ M, on MRC5 cells, in DMSO, in the following way.

MRC5 cells (human lung (fibroblasts)) were cultured in Dulbecco's modified Eagle medium (DMEM) supplemented with: 25 mM of glucose, 10% (v/v) of fetal calf serum, 100 IU of penicillin, 100 µg/ml of streptomycin and 1.5 µg/ml of fungizone, and kept under 5% of $CO_2$ at 37° C.

96-well plates were seeded with 2100 MRC5 cells per well in 200 µl of medium. After 24 hours, each of the compounds dissolved in DMSO was added for 72 hours, at a final concentration of $10^{-4}$ M or $10^{-5}$ M in a fixed volume of DMSO. The controls received an equal volume of DMSO.

The viable cell number was measured at 490 nm with the MTS reagent (Promega), and, for each compound, the concentration causing 50% inhibition of cell growth, $IC_{50}$, was calculated.

The results, in terms of percentage inhibition of cell growth (±standard error), are shown in table 1 below.

TABLE 1

Percentage inhibition of MRC5 cell growth by the compound (IIa) in accordance with the invention and by the comparative compounds GR5 and GR24 at concentrations of $10^{-4}$M and $10^{-5}$M

| | Percentage inhibition of MRC5 cell growth | |
| --- | --- | --- |
| | $10^{-4}$M | $10^{-5}$M |
| GR5 | 66 ± 1 | 0 ± 2 |
| GR24 | 97 ± 1 | 0 ± 11 |
| (IIa) | 11 ± 5 | 7 ± 4 |

The above results clearly show that, at the concentration of $10^{-4}$ M, the compound in accordance with the invention (IIa) exhibits a cytotoxicity which is much lower than that of the comparative compounds GR5 and GR24.

Example 4

Study of the Biological Activity on the Inhibition of Branching in the Pea

To this effect, ramosus (rms1) hyperbranched pea (*Pisum sativum* L.) mutants, known to exhibit a number of branches very much higher than the number of branches in wild-type pea, and in particular at all the nodes of the plant, were used. Generally, in the pea, the first two scales are considered to be the first two nodes, the cotyledonary node being node 0.

The rms1 mutant is an "SMS" signal biosynthesis mutant, repressing branching of the plant.

Tests for activity on the inhibition of branching were carried out in the following way.

The strigolactone-deficient rms1 (ccd8) pea mutants described in Beveridge et al., 1997, were used for the test (M3T884 line derived from the Térèse variety).

1/ Experiment 1

The activity of the compounds (IIa), (II'd) and (II'e) in accordance with the invention and of the comparative compound GR24 was evaluated at respective doses of 10 nM, 100 nM and 1 µM, by treatment at node 3.

For this, solutions containing each compound to be tested in 1% acetone, 4% polyethylene glycol 1450 and 50% ethanol were used.

24 plants were sown per treatment. 8 days after sowing, the treatment was carried out on the axillary bud at node 3, by application of 10 µl of each solution to be tested, directly on the bud, by means of a micropipette. The lateral outgrowths at nodes 1 and 2 were removed in order to encourage the growth of the axillary buds at the higher nodes.

The sprouting of the axillary buds at node 3 was measured 8 days after the treatment, by means of a digital sliding caliper.

Figure 3:
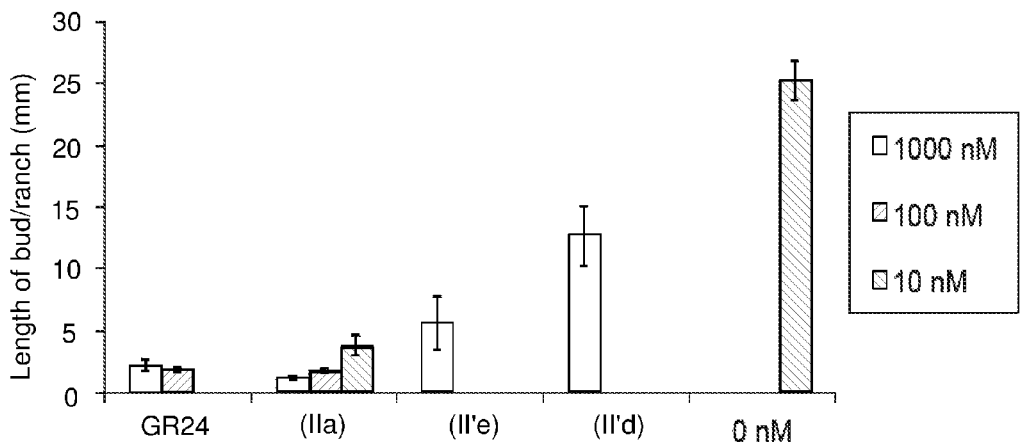
FIG. 3 represents a bar graph showing the activity, expressed in terms of length of bud/branch measured at node 3 8 days after treatment at node 3, of the compounds in accordance with the invention (IIa), (II'd) and (II'e) and of the comparative compound GR24, at doses of between 10 nM and 1 µM, on the repression of the branching of the pea mutant rms1.

The results, expressed as length of bud/branch 8 days after treatment with each compound, for each concentration tested, are shown in FIG. 3. The control without treatment (0 nM) is also represented in this figure.

It is observed therein that the compound (IIa) exhibits, at the highest concentrations, an inhibitory activity on bud growth which is greater than that of the comparative compound GR24. The compounds (II'd) and (II'e) also exhibit an inhibitory activity on bud growth at node 3, at the concentration of 1 µM.

2/ Experiment 2

The activity of the compounds (IIa), (IIb), (IIc), (II'd), (II'e) and (II'f) in accordance with the invention was evaluated at respective doses of 100 nM and 1 µM, by treatment at node 3.

For this, solutions containing each compound to be tested, in 1% acetone, 4% propylene glycol 1450 and 50% ethanol, were used.

24 plants were sown per treatment. 8 days after sowing, the treatment was carried out on the axillary bud at node 3, by application of 10 µl of each solution to be tested, directly on the bud, by means of a micropipette. The lateral outgrowths at nodes 1 and 2 were removed in order to encourage the growth of the axillary buds at the higher nodes.

The sprouting of the axillary buds at node 3 was measured 8 days after the treatment, by means of a digital sliding caliper.

Figure 4:
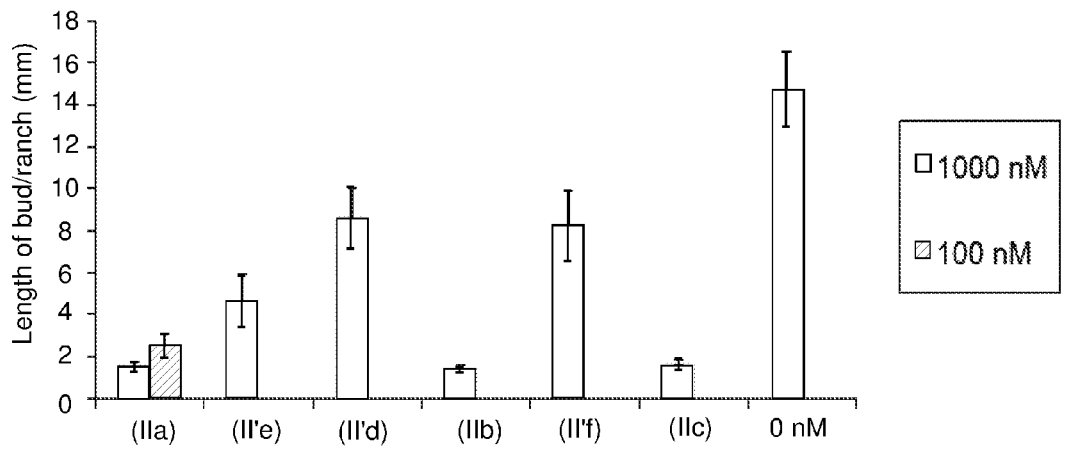
FIG. 4 represents a bar graph showing the activity, expressed in terms of length of bud/branch measured at node 3 8 days after treatment at node 3, of the compounds in accordance with the invention (IIa), (IIb), (IIc), (II'd), (II'e) and (II'f), at doses of between 100 nM and 1 µM, on the repression of the branching of the pea mutant rms1.

The results, expressed as length of bud/branch 8 days after treatment with each compound, for each concentration tested, are shown in FIG. 4. The control without treatment (0 nM) is also represented in this figure.

It is observed therein that all the compounds in accordance with the invention exhibit an inhibitory activity on bud growth at node 3. The compounds comprising a sulfur atom in the molecular (compounds (IIa), (IIb) and (IIc)) prove to be the most active.

3/ Experiment 3

The activity of the compounds (IIa), (IIIa), (IIIb) and (IIIc) in accordance with the invention, and also of GR24 as comparative compound, was evaluated at respective doses of 100 nM and 1 µM, by treatment at node 3, according to the protocol described above with reference to experiment 2.

A sample consisting only of the solvent, and without active compound, was also tested as negative control, termed "CTL 0".

Figure 5:
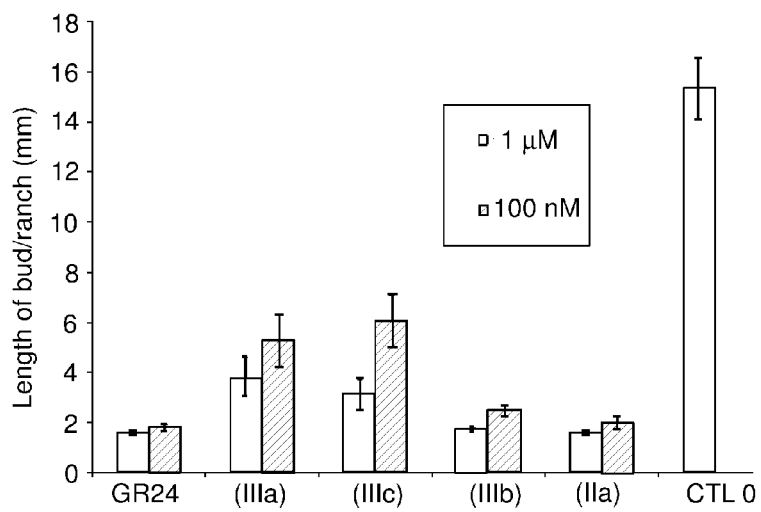
FIG. 5 represents a bar graph showing the activity, expressed in terms of length of bud/branch measured at node 3 8 days after treatment at node 3, of the compounds in accordance with the invention (IIa), (IIIa), (IIIb) and (IIIc), and of the comparative compound GR24, at respective doses of 100 nM and 1 µM, on the repression of the branching of the pea mutant rms1; a negative control "CTL 0" represents a sample consisting of the solvent alone.

The results, expressed in length of bud/branch 8 days after treatment with each compound, for each concentration tested, are shown in FIG. 5.

It is observed that the compounds (IIa) and (IIIb) in accordance with the invention exhibit an activity similar to that of the comparative compound GR24. The compounds (IIIa) and (IIIc), although slightly less active, exhibit, however, a high activity in terms of bud growth inhibition.

4/ Experiment 4

In this experiment, the activity of the compound (IIIa) in accordance with the invention, and also of GR24 as comparative compound, was evaluated at respective doses of 1 nM, 10 nM, 100 nM and 1 µM, by treatment at node 3, according to the protocol described above with reference to experiment 2, for doses of 10 nM, 100 nM and 1 µM of compounds.

A sample consisting only of the solvent, and without active compound ("CTL 0") was also tested as a negative control. A nontreated ("NT") control was also carried out.

Figure 6:
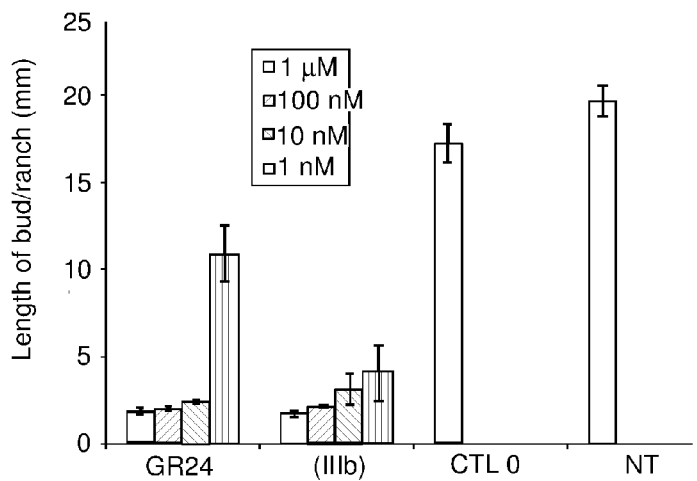
FIG. 6 represents a bar graph showing the activity, expressed in terms of length of bud/branch measured at node 3 8 days after treatment at node 3, of the compound in accordance with the invention (IIIb) and of the comparative compound GR24, at respective doses of 1 nM, 10 nM, 100 nM and 1 µM, on the repression of branching of the pea mutant rms1; a negative control "CTL 0" represents a sample consisting of the solvent alone, and a negative control "NT" represents a nontreated plant.

The results, expressed as length of bud/branch 8 days after treatment with each compound, for each concentration tested, are shown in FIG. 6.

It is observed therein that the compound (IIIb) in accordance with the invention exhibits a greater activity than that of the comparative compound GR24, in particular at the lowest doses.

5/ Experiment 5

A dose-response test for evaluating the activity of the compounds by deposition at node 3 was carried out according to the protocol described above with reference to experiment 2, for the compound in accordance with the invention (IIa) and for the comparative compounds GR24, Comp. 3 and Comp. 4. Concentrations of 10 nM, 100 nM and 1 µM were tested.

A sample consisting only of the solvent, and without active compound ("CTL 0"), was also tested as a negative control. A nontreated ("NT") control was also carried out.

Figure 7:
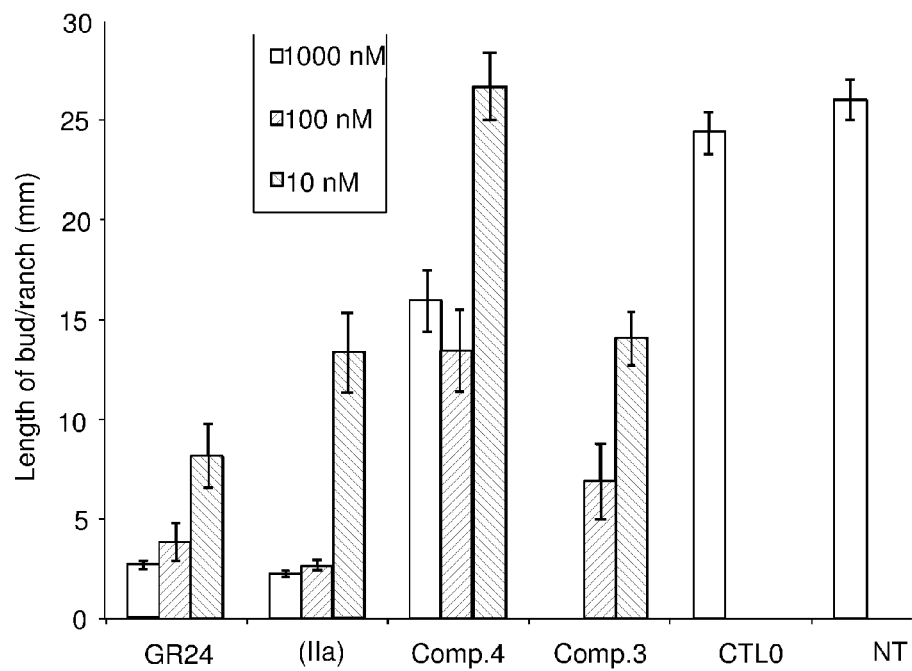
FIG. 7 represents a bar graph showing the activity, expressed in terms of length of bud/branch measured at node 3 8 days after treatment at node 3, of the compound in accordance with the invention (IIa) and of the comparative compounds GR24, Comp. 3 and Comp. 4, at respective doses of 10 nM, 100 nM and 1 µM, on the repression of the branching of the pea mutant rms1; a negative control "CTL 0" represents a sample consisting of the solvent alone, and a negative control "NT" represents a nontreated plant.

The results obtained (mean data on 24 plants) are shown in FIG. 7. It is observed therein that the compound in accordance with the invention (IIa) exhibits an activity which is greater than the comparative compounds provided by the prior art, Comp. 3 and Comp. 4, this being at all the doses tested.

6/ Experiment 6

A dose-response test for evaluating the activity of the compounds by deposition at node 3 was carried out according to the protocol described above with reference to experiment 2, for the compound in accordance with the invention (IIa) and for the comparative compounds GR24, Comp. 5 and Comp. 6. Concentrations of 10 nM and 100 nM were tested.

A sample consisting only of the solvent, and without active compound ("CTL 0"), was also tested as a negative control. A nontreated ("NT") control was also carried out.

Figure 8:
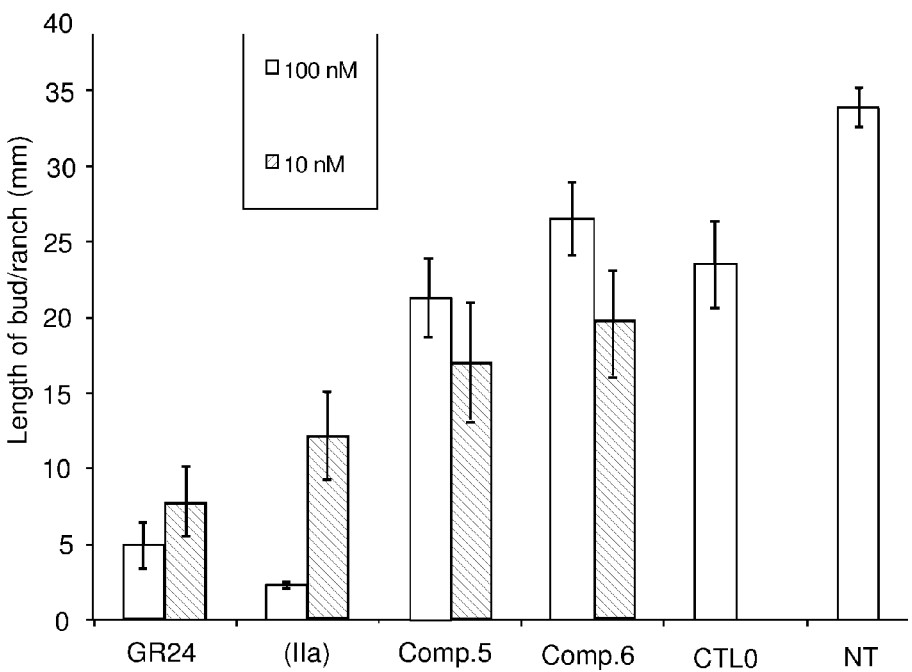
FIG. 8 represents a bar graph showing the activity, expressed in terms of length of bud/branch measured at node 3 8 days after treatment at node 3, of the compound in accordance with the invention (IIa) and of the comparative compounds GR24, Comp. 5 and Comp. 6, at respective doses of 10 nM and 100 nM, on the repression of the branching of the pea mutant rms1; a negative control "CTL 0" represents a sample consisting of the solvent alone, and a negative control "NT" represents a nontreated plant.

The results obtained (mean data on 24 plants) are shown in FIG. 8. It is observed therein that the compound in accordance with the invention (IIa) exhibits an activity which is greater than the comparative compounds provided by the prior art, Comp. 5 and Comp. 6, this being at all the doses tested.

7/ Experiment 7

The activity of the compound (IIa) in accordance with the invention on bud growth at node 4 was evaluated at doses respectively of 0.1 nM, 1 nM, 10 nM and 100 nM, by treatment at node 4. The GR24 compound was tested at the same concentrations, as comparative compound.

For this, solutions containing each compound to be tested, in 1% acetone, 4% polyethylene glycol 1450 and 50% ethanol, were used.

24 plants were sown per treatment. 8 days after sowing, the treatment was carried out on the axillary bud at node 4, by application of 10 µl of each solution to be tested, directly on the bud, by means of a micropipette. The lateral outgrowths at nodes 1 and 2 were removed in order to encourage the growth of the axillary buds at the higher nodes.

The sprouting of the axillary buds at node 4 was measured 8 days after the treatment by means of a digital sliding caliper.

Figure 9:
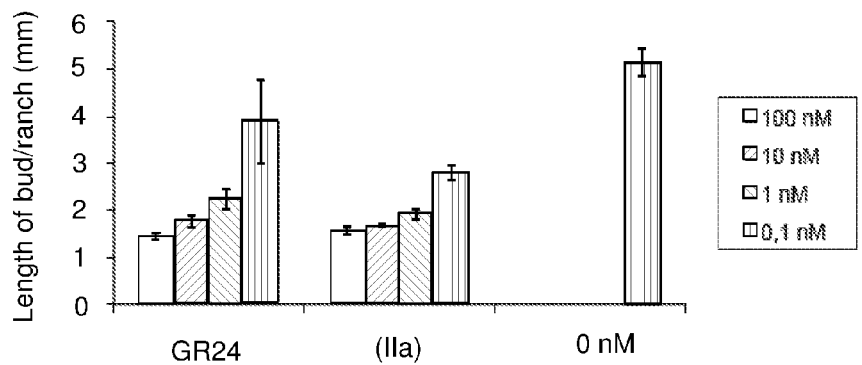
FIG. 9 represents a bar graph showing the activity, expressed in terms of length of bud/branch measured at node 4 8 days after treatment at node 4, of the compound (IIa) and of the comparative compound GR24 at doses of between 0.1 nM and 100 nM, on the repression of the branching of the pea mutant rms1.

The results, expressed as length of bud/branch 8 days after treatment with each compound, for each concentration tested, are shown in FIG. 9. The control without treatment (0 nM) is also represented in this figure.

It is observed therein that the compound (IIa) in accordance with the invention exhibits, after treatment at node 4, an inhibitory activity on bud growth at node 4 which is equivalent to that of GR24 at the strongest concentrations, and slightly better at the lowest concentration of 0.1 nM.

8/ Experiment 8

The activity of the compound (IIIa) in accordance with the invention on bud growth at node 3 was evaluated at a dose of 1000 nM by treatment at node 3. The GR24 compound was tested at the same concentration as comparative compound.

For this, solutions containing each compound to be tested, in 1% acetone, 4% polyethylene glycol 1450 and 50% ethanol, were used.

24 plants were sown per treatment. 8 days after sowing, the treatment was carried out on the axillary bud at node 3, by application of 10 µl of each solution to be tested, directly on the bud, by means of a micropipette. The lateral outgrowths at nodes 1 and 2 were removed in order to encourage the growth of the axillary buds at the higher nodes.

The sprouting of the axillary buds at node 3 was measured 8 days after the treatment by means of a digital sliding caliper.

Figure 10:
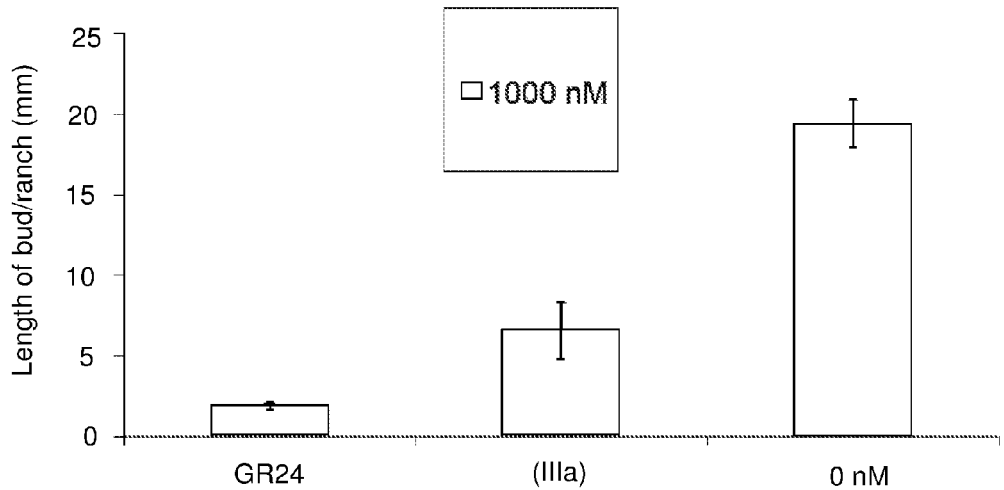
FIG. 10 represents a bar graph showing the activity, expressed in terms of length of bud/branch measured at node 3 8 days after treatment at node 3, of the compound in accordance with the invention (IIIa) and of the comparative compound GR24 at a dose of 1 µM, on the repression of the branching of the pea mutant rms1.

The results, expressed as length of bud/branch 8 days after treatment with each compound, for each concentration tested, are shown in FIG. 10. The control without treatment (0 nM) is also represented in this figure.

It is observed that the compound (IIIa) in accordance with the invention exhibits, after treatment at node 3, an inhibitory activity on bud growth at node 3 which, although less than that of GR24, is highly significant.

Example 5

Hydroponic Culture Test in Pea

For this example, ramosus (rms1) hyperbranched pea (*Pisum sativum* L.) mutants were used.

More particularly, rms1 (rms1-10) hyperbranched mutant plants were used. The nutritive solution (100%) was prepared by adding the following macronutrients to 1000 l of water: $HNO_3$ (0.28 l), $(NH_4)_2HPO_4$ (120 g), $Ca(NO_3)_2$ (40 g), $Mg(NO_3)_2$ (140 g), $KNO_3$ (550 g), $(NH_4)_2MoO_4$ (0.05 g), $H_3BO_3$ (15 g), $MnSO_4.H_2O$ (2 g), $ZnSO_4.7H_2O$ (1 g), $CuSO_4.5H_2O$ (0.25 g), Sequestrene® (10 g) (Fe-EDTA solution). The pea seeds were germinated in moist sand for 6 days, then placed in holes of a lid (35 holes/lid, 20 mm in diameter) of an opaque PVC pot containing the hydroponic culture solution (47 l, pH 5.8).

In a first experiment, acetone or the compound to be tested (dissolved in acetone) was added to the hydroponic culture solution so as to obtain a final concentration of 0 or 1 µM of compound to be tested and 0.01% of acetone.

The hydroponic culture solution was continually aerated by means of an aquarium pump and replaced each week. 8 days after the start of the treatment, the lengths of bud/branch (nodes 1 to 6) were measured with an electronic sliding caliper.

This experiment was carried out for the compounds according to the invention (IIa) and (IIIb), and also the GR24 compound as comparative compound. A negative control (<<CTL 0>>), corresponding to a treatment with the solvent alone, was also carried out.

Figure 11:
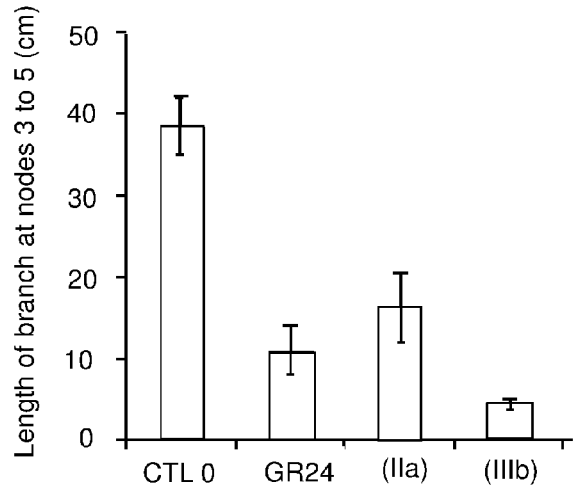
FIG. 11 shows a bar graph showing the activity, expressed in terms of length of branch measured at nodes 3 to 5, 8 days after the start of a hydroponic culture of pea rms1 mutants, in the presence of the compounds in accordance with the invention (IIa) and (IIIb) and of the comparative compound GR24 at a dose of 1 µM; a negative control "CTL 0" represents a sample consisting of the solvent alone.
Figure 12:
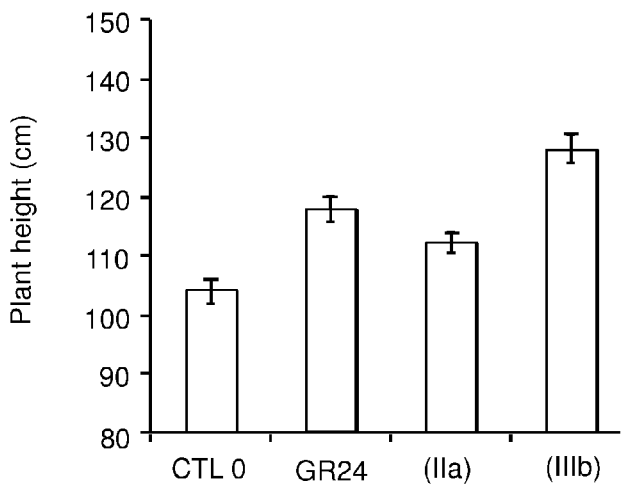
FIG. 12 shows a bar graph showing the activity, expressed in terms of plant height, 8 days after the start of a hydroponic culture of pea rms1 mutants, in the presence of the compounds in accordance with the invention (IIa) and (IIIb) and of the comparative compound GR24 at a dose of 1 µM; a negative control "CTL 0" represents a sample consisting of the solvent alone.

The results (mean data on 20 plants), in terms of, on the one hand, length of the branches at nodes 3 to 5 and, on the other hand, plant height, are shown respectively in FIGS. 11 and 12.

These results demonstrate the activity of the compounds in accordance with the invention (IIa) and (IIIb) on all the branches of nodes 3 to 5. A significant effect on plant height is also demonstrated, comparable between the comparative compound GR24 and the compound in accordance with the invention (IIa), and greater for the compound in accordance with the invention (IIIb).

The same experiment was carried out for the compound in accordance with the invention (II"g) and the comparative compound GR24. Dimethyl sulfoxide (DMSO) or the compound to be tested, dissolved in DMSO, was added to the hydroponic culture solution so as to obtain a final concentration of 0 or 3 μM of compound to be tested and 0.01% of DMSO.

Figure 13:
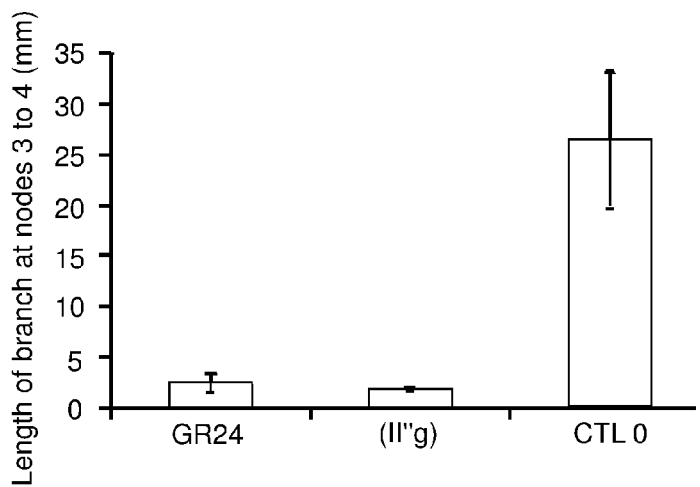
FIG. 13 shows a bar graph showing the activity, expressed in terms of length of branch measured at nodes 3 to 4, 8 days after the start of a hydroponic culture of pea rms1 mutants, in the presence of the compound in accordance with the invention (II"g) and of the comparative compound GR24 at a dose of 3 µM; a negative control "CTL 0" represents a sample consisting of the solvent alone.
Figure 14:
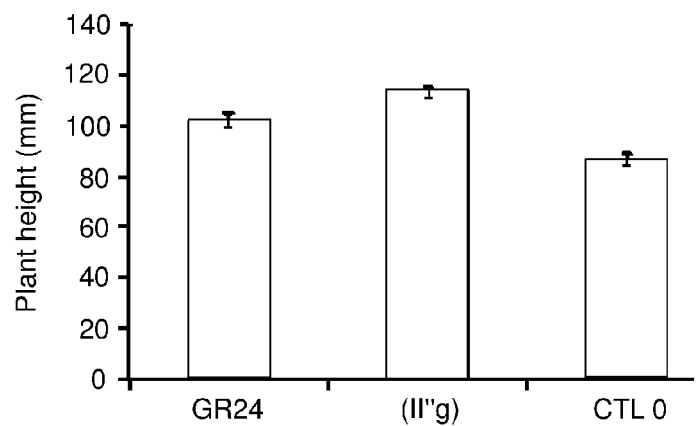
FIG. 14 shows a bar graph showing the activity, expressed in terms of plant height, 8 days after the start of a hydroponic culture of pea rms1 mutants, in the presence of the compound in accordance with the invention (II"g) and of the comparative compound GR24 at a dose of 3 µM; a negative control "CTL 0" represents a sample consisting of the solvent alone.

The results (mean data on 10 to 12 plants), in terms, on the one hand, of length of the branches at nodes 3 to 4 and, on the other hand, of plant height, are shown respectively in FIGS. 13 and 14.

These results demonstrate, for the compound in accordance with the invention (II"g), an activity on all the branches of nodes 3 to 4, and also an effect on plant height, which are both greater than those of the comparative compound GR24.

Example 6

Study of Toxicity in Pea

In this example, the toxicity of the compounds in accordance with the invention (IIa) and (IIIb), and of the comparative compound GR24, was evaluated by deposition at node 3 on hyperbranched rms4 mutant plants described in the publication by Johnson et al. (1997) and which do not respond to the hormonal action of strigolactones (M3T-946 line derived from the Térèse variety).

The protocol used is in accordance with that described in example 4 above. Compound concentrations of 100 nM and 3 μM were tested. A negative control consisting of the solvent alone («CTL 0») was also tested.

The number of dead buds following the treatment with 3 μM of compound was also determined after 8 days of treatment (on groups of 48 plants).

Figure 15:
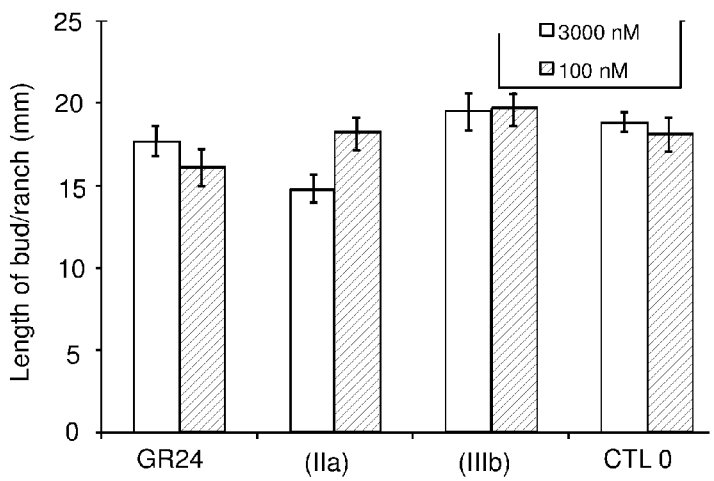
FIG. 15 represents a bar graph showing the activity, expressed in terms of length of bud/branch measured at node 3 8 days after treatment at node 3, of the compounds in accordance with the invention (IIa) and (IIIb), and of the comparative compound GR24, at respective doses of 100 nM and 3 µM, on the repression of the branching of the pea rms4 mutant; a negative control "CTL 0" represents a sample consisting of the solvent alone.
Figure 16:
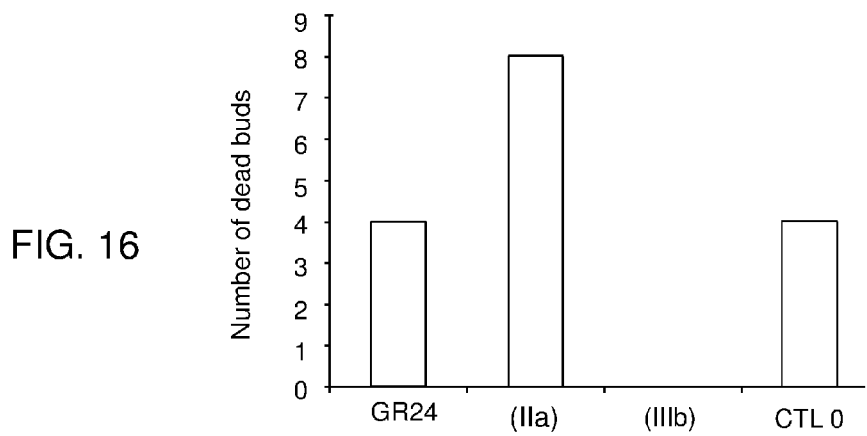
FIG. 16 shows a bar graph representing the number of dead buds for groups of 48 pea rms4 mutant plants, 8 days after treatment at node 3 with the compounds in accordance with the invention (IIa) and (IIIb), and the comparative compound GR24, at doses of 3 µM; a negative control "CTL 0" represents a sample consisting of the solvent alone.

The results obtained are shown in FIG. 15, for the length of bud/branch at node 3, and in FIG. 16, for the number of dead buds after treatment. These results demonstrate the absence of effects of the compounds in accordance with the invention (IIa) and (IIIb) compared with a negative control, and between the two treatment doses. In the same way, no significant difference is notable regarding the number of dead buds following the treatment. In particular, the treatment with the compound (IIIb) did not cause the death of any bud.

Example 7

Study of the Germinative Activity on Parasitic Plants

In this example, the germinative activity of the compounds in accordance with the invention (IIa) and (IIIb) and of the comparative compound GR24 was evaluated on the parasitic plants: *Orobanche cumana*, *Orobanche minor*, *Striga hermonthica*, *Phelipanche ramosa* (pv T and pv C).

The test protocol used was the following.

Two populations of *Phelipanche ramosa* were used in this study, pathovar (pv) C and T, described in the publication by Benharrat et al. (2005). Seeds of *Phelipanche ramosa* pathovar C were collected at Saint Martin de Fraigneau, France, on broomrapes parasitizing winter oilseed rape (*Brassica napus* L.) in 2005 and seeds of *Phelipanche ramosa* pathovar T were collected in Sarthe, France, on broomrapes developing on hemp (*Cannabis sativa* L.) in 2007.

Seeds of *Orobanche cumana* Wallr. were collected from broomrapes parasitizing sunflower (*Helianthus annuus* L.), at Longeville-sur-mer, France, in 2009; seeds of clover broomrape (*Orobanche minor* Sm.) from a parasite of red clover (*Trifolium pratense* L.) were obtained from Professor K. Yoneyama (Utsunomiya University, Japan).

Seeds of *Striga hermonthica* (Del.) Benth were collected at Gadarif, Eastern Sudan, in 1999.

The seeds are stored dry in the dark at 25° C.

The compounds to be studied were resuspended in acetone at 10 mmol·l$^{-1}$, then diluted with water to 1 mmol·l$^{-1}$ (water/acetone; v/v; 99/1). Dilutions of $1 \times 10^{-3}$ mol·l$^{-1}$ to $1 \times 10^{-15}$ mol·l$^{-1}$ were then prepared in a water/acetone mixture (v/v; 99/1). Seeds of parasitic plants were surface-sterilized according to the protocol described in the publication by Vieira Dos Santos et al. (2003), then resuspended in sterile water (10 g·l$^{-1}$) and distributed on a 96-well plate (in a proportion of 50 μl, i.e. approximately 100 seeds per well). After preconditioning (7 days, 21° C., in the dark, plate hermetically sealed, except for the seeds of *S. hermonthica*, which were preconditioned at 30° C.), the compounds to be studied were added and the volumes adjusted to 100 μl with water (water/acetone; v/v; 999/1).

In a plate, a range of concentrations from $10^{-13}$ mol·l$^{-1}$ to $10^{-6}$ mol·l$^{-1}$ was applied for GR24 and (IIa) and from $10^{-12}$ to $10^{-5}$ mol·l$^{-1}$ for (IIIb). Controls were carried out with a water/acetone mixture (v/v; 999/1) and without seeds. The plates were incubated so as to allow germination (21° C., in the dark or 30° C. for *Striga hermonthica*.). After 4 days, the seeds which had germinated were counted under a stereomicroscope (SZX10, Olympus). The seeds were considered to have germinated when the radicle was sticking out of the seed tegument. Each germination test was repeated at least 3 times. For each compound tested, dose-response curves (g=f(c), where g is the germination percentage and c the concentration (mol·l$^{-1}$)), and the EC$_{50}$ (median effective concentration) were modeled on the basis of a 4-parameter logistic curve calculated with SigmaPlot® 10.0.

Figure 17:
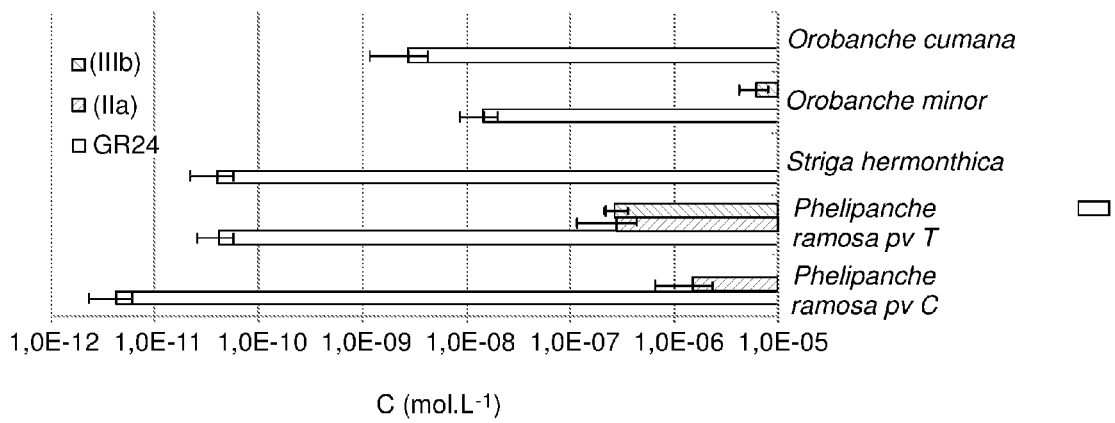
FIG. 17 is a bar graph showing, for the compounds in accordance with the invention (IIa) and (IIIb) and for the comparative compound GR24, the EC50 concentration in a test for germination of the parasitic plants: *Orobanche cumana, Orobanche minor, Striga hermonthica, Phelipanche ramosa* (pathovar pv T and pv C).

For each of the 3 compounds tested, the EC$_{50}$ concentration for each parasite thus obtained is shown in FIG. 17. It is observed therein that the compounds in accordance with the invention exhibit a very weak activity, much lower than that of GR24, on the germination of the seeds of parasitic plants, this being the case on the 4 parasites studied.

The percentages of maximum germination induced by the compounds tested for each parasitic plant were determined. These percentages are given in table 2 below.

TABLE 2

Percentage of maximum germination induced by the compounds for various parasitic plants

|  | GR24 | (IIa) | (IIIb) |
| --- | --- | --- | --- |
| *Phelipanche ramosa* pv C | 89 ± 6% | 27 ± 4% | no |
| *Phelipanche ramosa* pv T | 87 ± 7% | 72 ± 2% | 88 ± 6% |
| *Striga hermonthica* | 57 ± 5% | no | no |
| *Orobanche minor* | 81 ± 5% | no | 60 ± 6% |
| *Orobanche cumana* | 78 ± 5% | no | no | no: no significant germination compared to the negative control (<2%)

The compounds in accordance with the invention advantageously exhibit an activity on the germination of the parasitic plants which is much weaker than the comparative compound GR24 provided by the prior art.

The set of results above demonstrates that the compounds according to the invention, and in particular the compounds corresponding to formulae (IIa) and (IIIb), have a biological activity for the control of branching which is comparable to that of natural strigolactones and to the synthetic analogs GR24 and GR5 of the prior art, while at the same time being much easier to prepare than these synthetic analogs and exhibiting less cytotoxicity. These compounds according to the invention also make it possible to dissociate the activity on branching and that on the germination of broomrape and of *Striga hermonthica*.

The description above clearly shows that, by virtue of its various characteristics and their advantages, the present invention achieves the objectives that it set itself. In particular, it provides compounds which are simple to synthesize and which exhibit a considerable biological activity of branching inhibition in higher plants, so that the treatment of such plants with these compounds makes it possible to control their growth and their architecture entirely optimally, what is more by means of low amounts of compound, with a view to improving crop yield.

LITERATURE REFERENCES

Benharrat et al. (2005) Virulence diversity among branched broomrape (o-ramosa 1.) populations in France. Agron Sustainable Dev 25(1):123-128

Beveridge et al. (1997) The rms1 mutant of pea has elevated indole-3-acetic acid levels and reduced root-sap zeatin riboside content but increased branching controlled by graft-transmissible signal(s). Plant Physiol. 115: 1251-1258

Canevet et al. (1978) Friedel-Crafts Reaction of Aromatic Derivatives with 1,4-Dicarbonyl-2,3-Ethylenic Compounds 0.2. Alkylations by Some 5-Hydroxy or 5-Chloro-2,5-Dihydro-2-Furannones—New Method for Synthesis of 1h-Indene-1-Carboxylic Acids. Tetrahedron 34: 1935-1942

Dos Santos et al. (2003) Defense gene expression analysis of *Arabidopsis thaliana* parasitized by *Orobanche ramosa*. Phytopathology 93: 451-457

Fukui et al. (2011) New branching inhibitors and their potential as strigolactone mimics in rice. Bioorg. Med. Chem. Lett. 21: 4905-4908

Johnson et al. (1981) The Preparation of Synthetic Analogs of Strigol. Journal of the Chemical Society-Perkin Transactions 1: 1734-1743

Johnson et al. (2006) Branching genes are conserved across species. Genes controlling a novel signal in pea are coregulated by other long-distance signals. Plant Physiol. 142: 1014-1026

Mangnus et al. (1992) Improved Synthesis of Strigol Analog GR24 and Evaluation of the Biological-Activity of Its Diastereomers. J. Agric. Food Chem. 40:1230-1235

Nair et al. (1981) Degenerative chemistry of malondialdehyde—structure, stereochemistry, and kinetics of formation of enaminals from reaction with amino-acids. J. Am. Chem. Soc. 103: 3030-3036

Timonen et al. (2011) Synthesis and anti-inflammatory effects of a series of novel 7-hydroxycoumarin derivatives. Eur. J. Med. Chem. 46: 3845-3850.

The invention claimed is:
1. A compound of general formula (I):

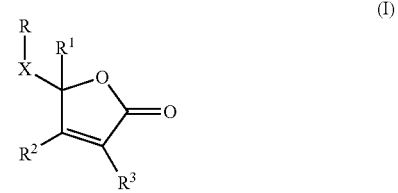

in which:
X represents an oxygen atom, a sulfur atom, NH or an N-alkyl radical,
$R^1$ and $R^2$ are identical or different, each representing a hydrogen atom or a linear or branched, saturated or unsaturated, $C_1$-$C_{10}$ hydrocarbon-based radical, provided that $R^1$ and $R^2$ not both representing a hydrogen atom,
$R^3$ represents a linear or branched, saturated or unsaturated, $C_1$-$C_{10}$ hydrocarbon-based radical, and
R represents a phenyl radical monosubstituted with a substituent Y chosen from Cl, Br, I and $CF_3$, or a phenyl radical disubstituted with a substituent Y and a substituent Z, Y and Z, which are identical or different, being each chosen from Cl, Br, I and $CF_3$, or forming together a saturated or unsaturated or aromatic, optionally substituted, ring which may contain one or more heteroatoms, or
R represents a radical:

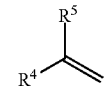

where $R^4$ represents a linear or branched, saturated or unsaturated, $C_1$-$C_{15}$ hydrocarbon-based radical, and
$R^5$ represents a linear or branched, saturated or unsaturated, $C_1$-$C_{10}$ hydrocarbon-based radical, optionally substituted, a $COR^6$ group or a $CO_2R^6$ group, where $R^6$ represents a hydrogen atom or a linear or branched, saturated or unsaturated, $C_1$-$C_{10}$ hydrocarbon-based radical.

2. The compound as claimed in claim 1, wherein $R^3$ represents a linear $C_1$-$C_{10}$ alkyl radical.

3. The compound as claimed in claim 2, wherein $R^3$ represents a methyl radical.

4. The compound as claimed in claim 1, wherein $R^1$ and $R^2$ each represent a hydrogen atom or a linear or branched $C_1$-$C_{10}$ alkyl radical.

5. The compound as claimed in claim 4, wherein $R^1$ represents a hydrogen atom and $R^2$ represents a linear or branched $C_1$-$C_{10}$ alkyl radical.

6. The compound as claimed in claim 5, wherein $R^2$ represents a methyl radical.

7. The compound as claimed in claim 1, wherein X represents a sulfur atom or an oxygen atom.

8. The compound as claimed in claim 1, wherein R represents a phenyl radical substituted at least in the para-position.

9. The compound as claimed in claim 1, of general formula (II):

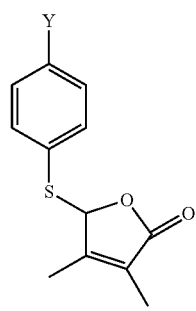

(II)

in which Y is chosen from Cl, Br, I and CF$_3$.

10. The compound as claimed in claim 9, in which Y is a chlorine atom.

11. The compound as claimed in claim 1, of general formula (II″):

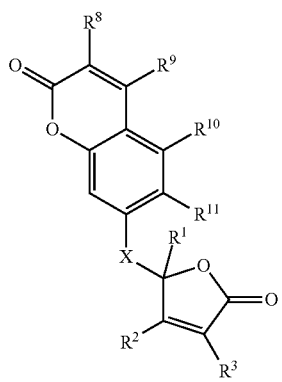

(II″)

in which:

X represents an oxygen atom, a sulfur atom, NH or an N-alkyl radical,

R$^1$ and R$^2$ are identical or different, each representing a hydrogen atom or a linear or branched, saturated or unsaturated, C$_1$-C$_{10}$ hydrocarbon-based radical, provided that R$^1$ and R$^2$ not both representing a hydrogen atom, R$^3$ represents a linear or branched, saturated or unsaturated, C$_1$-C$_{10}$ hydrocarbon-based radical, R$^8$, R$^9$, R$^{10}$ and R$^{11}$, which are identical or different, each representing a hydrogen atom, Cl, Br, I, CF$_3$, CHO, CN, NO$_2$, a linear or branched, saturated or unsaturated, optionally substituted, hydrocarbon-based radical, or a CO$_2$R$^{12}$ group, where R$^{12}$ represents a hydrogen atom or a linear or branched, saturated or unsaturated C$_1$-C$_{10}$ hydrocarbon-based radical.

12. The compound as claimed in claim 11, wherein R$^{12}$ represents a linear or branched, saturated or unsaturated, C$_1$-C$_{10}$ hydrocarbon-based radical.

13. The compound as claimed in claim 11, of general formula (II″) in which R$^8$, R$^9$, R$^{10}$ and R$^{11}$ each represent a hydrogen atom.

14. The compound as claimed in claim 1, wherein R represents a radical:

where R$^4$ represents a linear or branched C$_1$-C$_{15}$ alkyl radical or alkenyl radical, and R$^5$ represents a linear or branched, C$_1$-C$_{10}$, optionally substituted, hydrocarbon-based radical, a COR$^6$ group or a CO$_2$R$^6$ group, where R$^6$ represents a linear or branched, C$_1$-C$_{10}$hydrocarbon-based radical.

15. The compound as claimed in claim 14, wherein R$^5$ represents a linear or branched, C$_1$-C$_5$, optionally substituted, hydrocarbon-based radical.

16. The compound as claimed in claim 14, wherein R$^5$ represents a COR$^6$ group or a CO$_2$R$^6$ group, where R$^6$ represents a linear or branched C$_1$-C$_5$ hydrocarbon-based radical.

17. The compound as claimed in claim 14, in which R$^5$ represents a linear or branched, C$_1$-C$_{10}$ hydrocarbon-based radical, which is substituted with an electron-withdrawing group.

18. The compound as claimed in claim 17, in which R$^5$ represents a linear or branched unsaturated C$_1$-C$_{10}$ hydrocarbon-based radical, which is substituted with an electron-withdrawing group.

19. The compound as claimed in claim 17, in which R$^5$ represents a linear or branched C$_1$-C$_5$ hydrocarbon-based radical which is substituted with an electron-withdrawing group.

20. The compound as claimed in claim 17, in which R$^5$ represents a linear or branched C$_1$-C$_{10}$ hydrocarbon-based radical, which is substituted at its free end with an electron-withdrawing group.

21. The compound as claimed in claim 17, wherein said electron-withdrawing group is chosen from: CHO, CN, NO$_2$ and CO$_2$R$^7$, where R$^7$ represents a linear or branched, C$_1$-C$_{10}$ hydrocarbon-based radical.

22. The compound as claimed in claim 21, wherein R$^7$ represents a linear or branched C$_1$-C$_5$ hydrocarbon-based radical.

23. A composition for the treatment of higher plants, comprising a compound as claimed in claim 1.

24. The composition as claimed in claim 23, wherein the concentration of said compound is between 0.1 and 1000 nM.

25. The composition as claimed in claim 24, wherein the concentration of said compound is between 1 and 100 nM.

26. The use of a compound as claimed in claim 1, for the treatment of a higher plant with a view to controlling the growth and the architecture of said plant.

27. The use as claimed in claim 26, wherein an appropriate amount of said compound is brought into contact with the plant so as to inhibit the formation of at least one branch.

28. The use as claimed in claim 27, wherein a composition comprising said compound is applied to an at least partial portion of the aerial part of the plant.

29. The use as claimed in either of claim 27, wherein a composition comprising said compound is applied to axillary buds of the plant.

30. The use as claimed in claim 27, wherein a composition comprising said compound is injected into an aerial part of said plant.

31. The use as claimed in claim 27, wherein a composition comprising said compound is introduced via at least one root of said plant.

32. The use as claimed in claim 27, wherein the concentration of said compound in said composition is between 0.1 and 1000 nM.

33. The use as claimed in claim 32, wherein the concentration of said compound in said composition is between 1 and 100 nM.

* * * * *